United States Patent
Mori

(10) Patent No.: US 9,250,215 B2
(45) Date of Patent: Feb. 2, 2016

(54) ULTRASONIC WAVE DETECTION APPARATUS, RECORDING MATERIAL DETERMINATION APPARATUS, AND IMAGE FORMING APPARATUS

(75) Inventor: Atsunobu Mori, Suntou-gun (JP)

(73) Assignee: Canon Kabushiki Kaisha, Toyko (JP)

( * ) Notice: Subject to any disclaimer, the term of this patent is extended or adjusted under 35 U.S.C. 154(b) by 398 days.

(21) Appl. No.: 13/586,205

(22) Filed: Aug. 15, 2012

(65) Prior Publication Data

US 2013/0051818 A1    Feb. 28, 2013

(30) Foreign Application Priority Data

Aug. 22, 2011    (JP) .................................. 2011-180546

(51) Int. Cl.
| | |
|---|---|
| B65H 43/00 | (2006.01) |
| G01N 29/34 | (2006.01) |
| G03G 15/00 | (2006.01) |
| G01N 29/38 | (2006.01) |

(52) U.S. Cl.
CPC .............. *G01N 29/348* (2013.01); *G01N 29/38* (2013.01); *G03G 15/65* (2013.01); *B65H 2553/30* (2013.01); *B65H 2557/64* (2013.01); *G03G 2215/00637* (2013.01); *G03G 2215/00738* (2013.01)

(58) Field of Classification Search
CPC .............. B65H 2552/30; B65H 7/125; B65H 2511/524; B65H 2557/64; G03G 2215/00742; G03G 2215/00637; G03G 15/703; G03G 2215/00548; G03G 15/65; G01N 29/34; G01N 29/348; G01N 29/36; G01N 29/38; G01N 29/40; G01N 29/42; G01N 29/4409–29/4436

USPC ........................................................... 399/18
See application file for complete search history.

(56) References Cited

U.S. PATENT DOCUMENTS

| | | | | |
|---|---|---|---|---|
| 6,739,591 | B2 * | 5/2004 | Chujo et al. ................... | 271/262 |
| 7,130,245 | B2 * | 10/2006 | Okitsu et al. .................. | 367/125 |
| 2003/0006550 | A1 | 1/2003 | Chujo et al. | |
| 2009/0310992 | A1 * | 12/2009 | Iwasa et al. ..................... | 399/45 |

FOREIGN PATENT DOCUMENTS

| | | |
|---|---|---|
| CN | 101604131 A | 12/2009 |
| CN | 101604132 A | 12/2009 |
| JP | sho58-123452 A | 7/1983 |

(Continued)

*Primary Examiner* — Daniel J Colilla
*Assistant Examiner* — John M Royston
(74) *Attorney, Agent, or Firm* — Canon USA, Inc. I.P. Division

(57) ABSTRACT

An ultrasonic wave detection apparatus includes a transmission unit which transmits ultrasonic waves at a first frequency and a second frequency, a reception unit which receives ultrasonic waves transmitted from the transmission unit, and a control unit which causes the transmission unit to transmit ultrasonic waves at the first frequency and causes the reception unit to receive the first frequency ultrasonic waves to obtain a detection timing of a peak value of a n-th wave of the received first frequency ultrasonic waves, causes the transmission unit to transmit ultrasonic waves at the second frequency and causes the reception unit to receive the second frequency ultrasonic waves to obtain a detection timing of a peak value of a n-th wave of the received second frequency ultrasonic waves, and specifies "n" of the n-th wave from which the peak value is detected based on a difference in the detection timings.

22 Claims, 24 Drawing Sheets

(56) References Cited

FOREIGN PATENT DOCUMENTS

| | | |
|---|---|---|
| JP | 2004-085421 A | 3/2004 |
| JP | 2004-156917 A | 6/2004 |
| JP | 2004-231404 A | 8/2004 |
| JP | 2005-024428 A | 1/2005 |
| JP | 2007-024837 A | 2/2007 |
| JP | 2010-018433 A | 1/2010 |

* cited by examiner

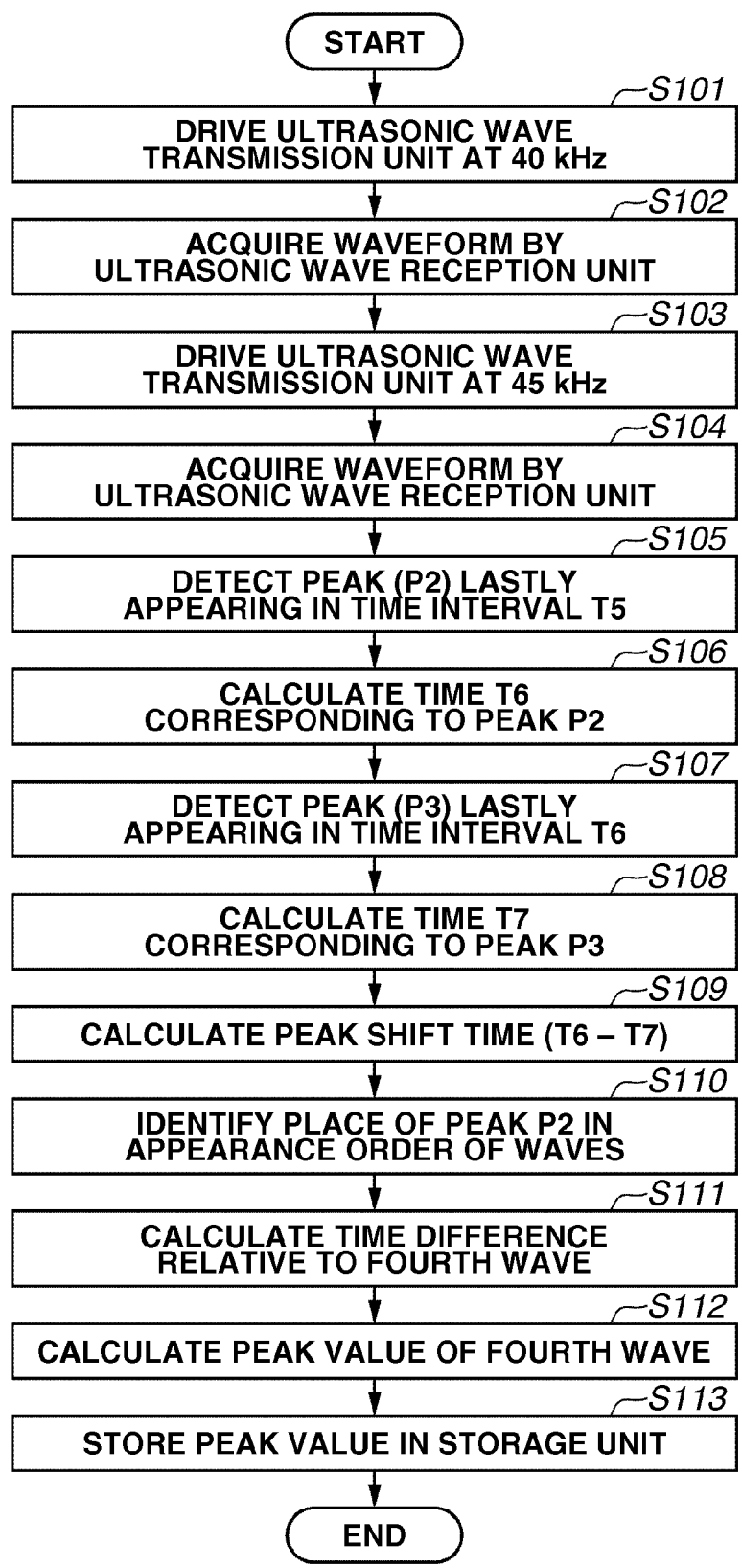

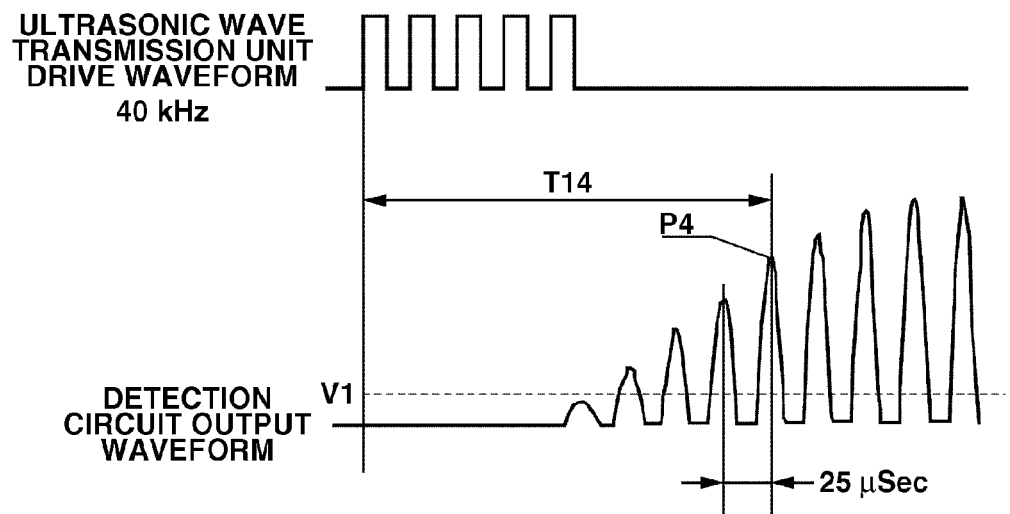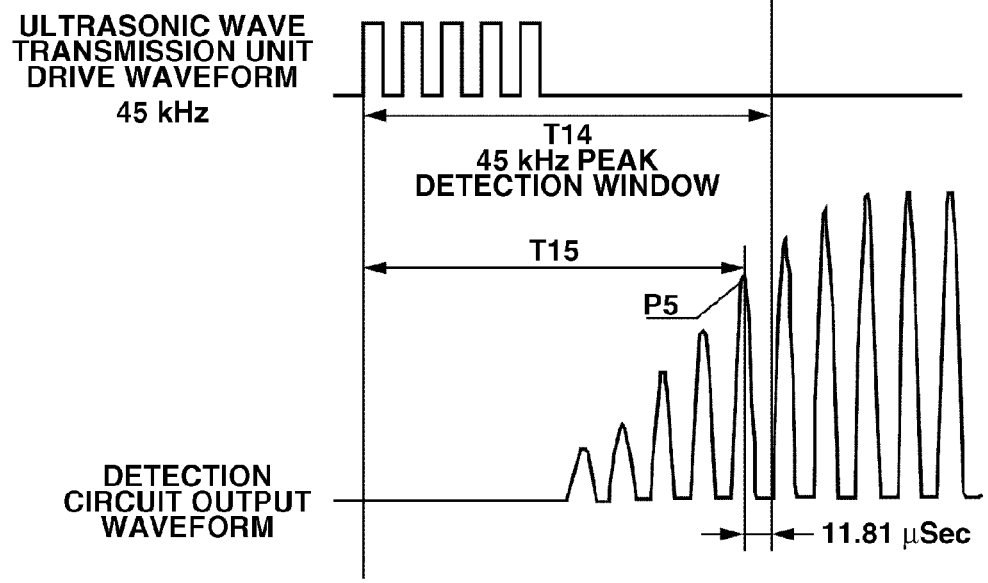

ULTRASONIC WAVE DETECTION APPARATUS, RECORDING MATERIAL DETERMINATION APPARATUS, AND IMAGE FORMING APPARATUS

BACKGROUND OF THE INVENTION

1. Field of the Invention

The present invention relates to an apparatus for detecting a characteristic of a recording material using an ultrasonic wave.

2. Description of the Related Art

A conventional image forming apparatus enables a user to set a type of a recording material (which may be referred to as "paper type") via an operation panel provided on as an external apparatus, such as a computer, or on the body of the image forming apparatus. The image forming apparatus can be controlled in such a way as to optimize image transfer conditions (e.g., bias, an image forming speed) and image fixing conditions (e.g., a quantity of heat, a recording material conveyance speed) according to the settings.

However, if a user forgets or fails in setting a type of a recording material, it is unable to optimize image forming conditions. A defective image may be generated. Therefore, to reduce a burden on a user or to appropriately control the image forming conditions according to a type or a state of a recording material, it is conventionally known that a recording material detection sensor can be provided in an image forming apparatus to automatically determine the type of the recording material.

More specifically, Japanese Patent Application Laid-Open No. 2007-24837 discusses a method in which a grammage of a recording material can be determined based on a transmittance value of an ultrasonic wave that penetrates through the recording material. Japanese Patent Application Laid-Open No. 2010-18433 discusses a method in which a rising waveform of an ultrasonic wave reception unit is used in grammage detection. When the method discussed in Japanese Patent Application Laid-Open No. 2010-18433 is employed, the grammage of a recording material can be accurately detected based on ultrasonic waves, while the positional variation of the recording material can be suppressed and reflections from members surrounding the sensor or environmental variations can be reduced.

According to the above-described detection method using ultrasonic waves discussed in Japanese Patent Application Laid-Open No. 2007-24837 or Japanese Patent Application Laid-Open No. 2010-18433, it is necessary to correct a change in the propagation speed of ultrasonic waves in an environment in which an ultrasonic wave detection apparatus is installed to accurately detect the grammage of a recording material. For example, to obtain the grammage of a recording material, a reception signal (P0) in a state where no recording material is present between an ultrasonic wave transmission unit and an ultrasonic wave reception unit and a reception signal (P1) in a state where a recording material is present between the ultrasonic wave transmission unit and the ultrasonic wave reception unit are obtained, and the grammage is detected based on a ratio of the reception signal P0 to the reception signal P1 (i.e., ratio P1/P0). The propagation speed of ultrasonic waves is variable depending on environmental factors. Therefore, to accurately obtain the detection timing of each of the reception signals P0 and P1, a correcting operation needs to be performed according to the propagation speed of ultrasonic waves considering the environmental factors.

SUMMARY OF THE INVENTION

Exemplary embodiments of the present invention are directed to a technique capable of accurately obtaining detection timing of a target ultrasonic wave without performing any correction operation considering environmental factors.

According to an aspect of the present invention, an ultrasonic wave detection apparatus includes a transmission unit configured to transmit ultrasonic waves at a first frequency and a second frequency, a reception unit configured to receive ultrasonic waves transmitted from the transmission unit, and a control unit configured to cause the transmission unit to transmit ultrasonic waves at the first frequency and cause the reception unit to receive the first frequency ultrasonic waves to obtain a detection timing of a peak value of a n-th wave of the received first frequency ultrasonic waves, configured to cause the transmission unit to transmit ultrasonic waves at the second frequency and cause the reception unit to receive the second frequency ultrasonic waves to obtain a detection timing of a peak value of a n-th wave of the received second frequency ultrasonic waves, and further configured to specify "n" of the n-th wave from which the peak value is detected based on a difference in the detection timings.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

FIG. 5 is a flowchart illustrating a control sequence for calculating a peak of the fourth wave according to a first exemplary embodiment of the present invention.

FIGS. 16A and 16B illustrate frequency changes in a waveform received when ultrasonic waves are transmitted at the 40 kHz frequency and in an output waveform received when ultrasonic waves are transmitted at the 45 kHz frequency according to the fourth exemplary embodiment.

DESCRIPTION OF THE EMBODIMENTS

Various exemplary embodiments, features, and aspects of the invention will be described in detail below with reference to the drawings.

Constituent components described in the following exemplary embodiments can be appropriately modified in their dimensions, materials, shapes, and relative layout considering the configuration and various conditions of an apparatus to which the present invention is applied. Accordingly, the scope of the present invention is not limited to the following exemplary embodiments unless it is specially mentioned.

Figure 1:
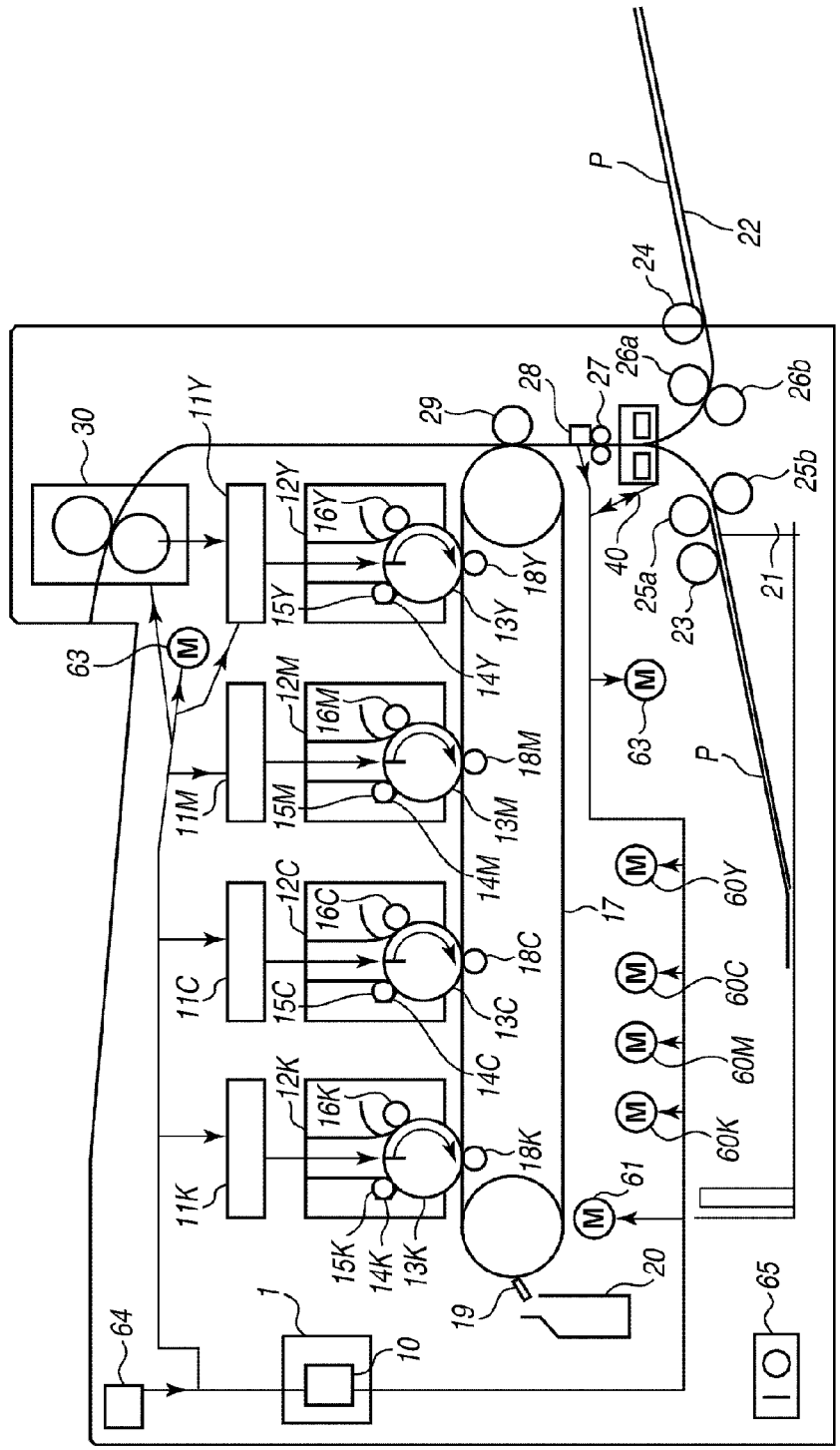
FIG. 1 illustrates a schematic configuration of an image forming apparatus according to an exemplary embodiment of the present invention.

An ultrasonic wave detection apparatus according to a first exemplary embodiment is, for example, usable for an image forming apparatus, such as a copy machine and a printer. FIG. 1 schematically illustrates an example configuration of an inline type color image forming apparatus as an example of the ultrasonic wave detection apparatus. The image forming apparatus includes the following configuration.

The inline type color image forming apparatus is configured to output a full-color image by overlapping four color toners of yellow (Y), magenta (M), cyan (C), and black (K). Further, the image forming apparatus includes laser scanners (11Y, 11M, 11C, 11K) and cartridges (12Y, 12M, 12C, and 12K) to form images of the respective colors. Each cartridge (12Y, 12M, 12C, or 12K) includes the following members. Each photosensitive drum (13Y, 13M, 13C, or 13K) rotates in a direction indicated by an arrow. Each photosensitive drum cleaner (14Y, 14M, 14C, or 14K) is provided in such a way as to be brought into contact with the corresponding photosensitive drum (13Y, 13M, 13C, or 13K). Further, the image forming apparatus includes charging rollers (15Y, 15M, 15C, and 15K) and developing rollers (16Y, 16M, 16C, and 16K). Each drum motor (60Y, 60M, 60C, or 60K) can drive the photosensitive drum 13, the charging roller 15, and the developing roller 16 of the corresponding color.

The photosensitive drums (13Y, 13M, 13C, and 13K) of the respective colors are disposed in such a way as to be brought into contact with an intermediate transfer belt 17 which is driven by an intermediate transfer belt driving motor 61. Each primary transfer roller (18Y, 18M, 18C, or 18K) is disposed at a position where the roller faces the corresponding photosensitive drum (13Y, 13M, 13C, or 13K) via the intermediate transfer belt 17. A belt cleaner 19 is provided near the intermediate transfer belt 17 to store the cleaned toners in a waste toner container 20.

A recording material P can be stored in a cassette 21 or a manual feeding tray 22. The recording material P stored in the cassette 21 can be conveyed by a paper feeding roller 23 and a pair of separation rollers 25a and 25b. A paper feeding motor 62 can drive the paper feeding roller 23. The recording material P stored in the manual feeding tray 22 can be conveyed by a paper feeding roller 24 and a pair of separation rollers 26a and 26b. A conveyance path of the cassette 21 and a conveyance path of the manual feeding tray 22 are merged into a common conveyance path at the downstream side of their separation rollers. A pair of registration rollers 27 is provided on the common conveyance path. A registration sensor 28 is provided at the downstream of the registration rollers 27 in the recording material conveyance direction. A secondary transfer roller 29 is disposed at the downstream side of the registration rollers 27 and is brought into contact with the intermediate transfer belt 17. A fixing device 30, which is driven by a fixing motor 63, is provided at the downstream side of the secondary transfer roller 29. An environment sensor 64 can measure an ambient temperature of the image forming apparatus. A power switch 65 is operable to turn on and off a power source of the image forming apparatus.

An engine controller 1 is operable as a control unit of the image forming apparatus. The engine controller 1 includes a control unit 10 and various input/output control circuits (not illustrated). The control unit 10 can control various operations to be performed by the image forming apparatus. More specifically, the control unit 10 can control the fixing motor 63, the intermediate transfer belt driving motor 61, the drum motors 60, the paper feeding motor 62, laser scanners 11, an ultrasonic wave detection apparatus 40, the environment sensor 64, and the like.

Next, electrophotographic processes are described. First, in the cartridge (12Y, 12M, 12C, or 12K), the charging roller (15Y, 15M, 15C, or 15K) uniformly charges the surface of the corresponding photosensitive drum (13Y, 13M, 13C, or 13K).

Next, the laser scanner (11Y, 11M, 11C, or 11K) irradiates the surface of the corresponding photosensitive drum (13Y, 13M, 13C, or 13K) with a laser beam that is modulated based on image data. An electrostatic latent image can be formed on the surface of the photosensitive drum (13Y, 13M, 13C, or 13K) by removing the electric charges of the portion that is irradiated with the laser beam. The developing rollers (16Y, 16M, 16C, and 16K) can form toner images of the respective colors on the surfaces of the corresponding photosensitive drums (13Y, 13M, 13C, and 13K) by supplying charged toners to the electrostatic latent images. The primary transfer rollers (18Y, 18M, 18C, and 18K) can successively transfer the toner images formed on the surfaces of the respective photosensitive drums (13Y, 13M, 13C, and 13K) to the intermediate transfer belt 17 so as to overlap the toner images.

The paper feeding roller 23 can convey the recording material P from the cassette 21 to the separation rollers 25a and 25b. When a plurality of sheets of the recording material P is conveyed, the separation rollers 25a and 25b conveys the recording material P one by one toward the registration rollers 27. The toner images on the intermediate transfer belt 17 can be transferred to the recording material P conveyed by the registration rollers 27 by applying a bias voltage to the secondary transfer roller 29. The fixing device 30 applies heat and pressure to the recording material P to fix the toner images formed thereon. The recording material P is then discharged from the fixing device 30 to the outside of the image forming apparatus. When the recording material P is fed from the manual feeding tray 22, the recording material P is processed similarly, thus, the description thereof is omitted.

Next, the ultrasonic wave detection apparatus is described below. The ultrasonic wave detection apparatus 40 is disposed on the conveyance path after the conveyance path from the cassette 21 merges with that from the manual feeding tray 22. The ultrasonic wave detection apparatus 40 includes an ultrasonic wave transmission unit 40a configured to transmit ultrasonic waves and an ultrasonic wave reception unit 40b configured to receive the ultrasonic waves, and detect the grammage or a double feed state of the recording material P based on the transmittance of the received ultrasonic wave. The ultrasonic wave detection apparatus that can be used to determine the type of the recording material P is operable as a recording material determination apparatus. In the context of the present application, a double feed state is when two or more sheets of recording material P, are being fed at the same time toward the registration rollers 27. It is feasible to apply an optimum bias voltage to the secondary transfer roller 29 or cause the fixing device 30 to thermally transfer and fix toner images based on the grammage obtained from the ultrasonic wave detected by the ultrasonic wave detection apparatus 40.

Figure 2:
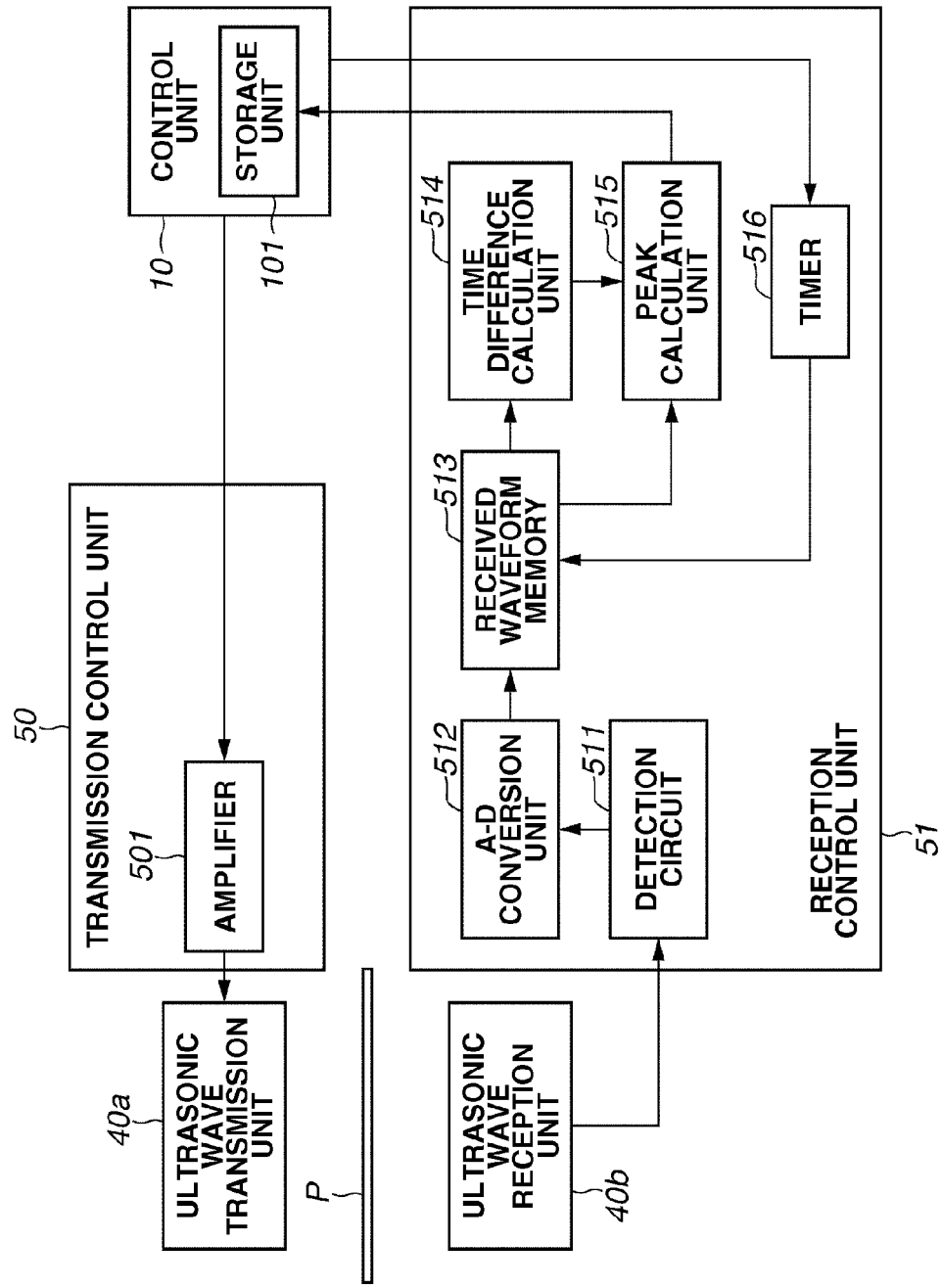
FIG. 2 is a control block diagram of an ultrasonic wave detection unit according to an exemplary embodiment.

A detection method performed by the ultrasonic wave detection apparatus 40 is described in detail below with reference to FIG. 2. FIG. 2 is a control block diagram of the ultrasonic wave detection apparatus 40. The ultrasonic wave transmission unit 40a can transmit ultrasonic waves to the recording material P. The ultrasonic wave reception unit 40b can receive the ultrasonic waves that have penetrated the recording material P. The ultrasonic wave transmission unit 40a and the ultrasonic wave reception unit 40b are disposed at predetermined positions across the conveyance path to detect the recording material P to be conveyed along the conveyance path. A transmission control unit 50 can drive the ultrasonic wave transmission unit 40a. A reception control unit 51 can detect a voltage signal that represents the ultrasonic waves received by the ultrasonic wave reception unit 40b and perform predetermined processing on the detected signal. The signal processed by the reception control unit 51 can be transmitted to the control unit 10. The control unit 10 can detect the grammage of the recording material P and the double feed state of the recording material P.

Sequential operations to detect the recording material P are performed in the following manner. When the control unit 10 transmits a driving signal to the transmission control unit 50, the control unit 10 resets a timer 516 of the reception control unit 51 and starts a counting operation. When the control unit 10 detects the grammage of the recording material P, the control unit 10 transmits rectangular waves of frequency 40 kHz/Duty 50% to the transmission control unit 50 for a time interval of 125 microseconds (μs) or (μsec). An amplifier 501 of the transmission control unit 50 amplifies a level of the driving signal (i.e., voltage value) and outputs the amplified signal to the ultrasonic wave transmission unit 40a. The ultrasonic wave transmission unit 40a thus outputs 40 kHz ultrasonic waves.

Figure 3:
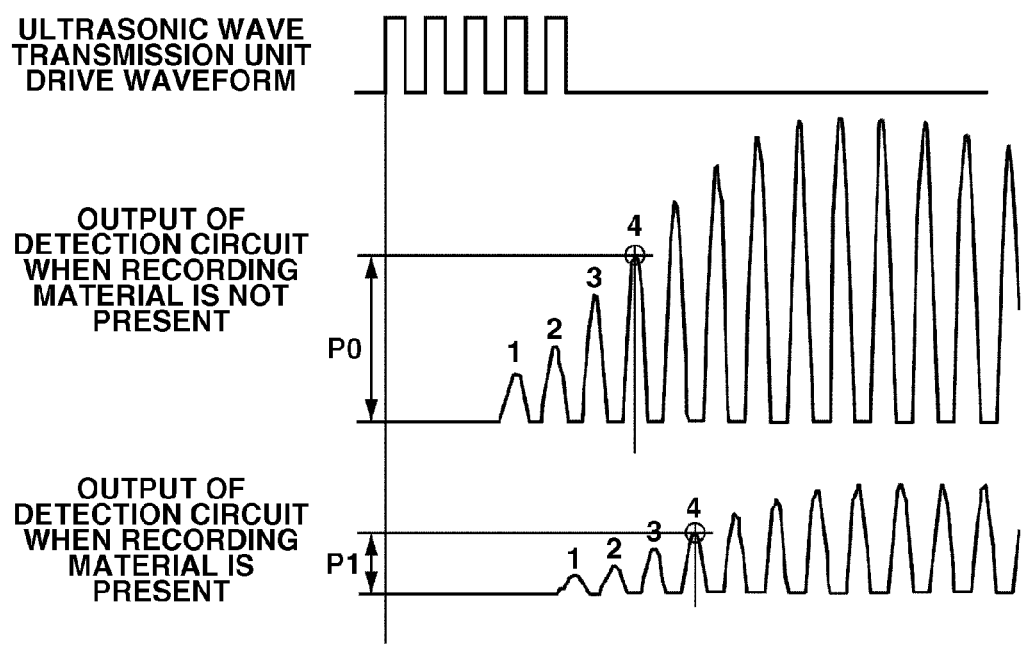
FIG. 3 illustrates an output waveform obtainable in a state where a recording material P is present in an intervenient space between an ultrasonic wave transmission unit and an ultrasonic wave reception unit, and an output waveform obtainable in a state where no recording material is present in the space.

The ultrasonic wave reception unit 40b can receive the ultrasonic waves transmitted from the ultrasonic wave transmission unit 40a or the ultrasonic waves having penetrated through the recording material P, and can output the received ultrasonic waves to a detection circuit 511 of the reception control unit 51. The detection circuit 511 has a function of amplifying the input signal and can perform half-wave rectification on the input signal. FIG. 3 illustrates output waveforms of the detection circuit 511, in which the upper waveform can be obtained when the recording material P is not present between the ultrasonic wave transmission unit 40a and the ultrasonic wave reception unit 40b, and the lower waveform can be obtained when the recording material P is present therebetween. As illustrated in FIG. 3, the waves output from the detection circuit 511 has a half-wave rectified sine waveform whose amplitude increases as the time elapses.

To accurately detect the grammage, it is necessary to extract a peak value of a predetermined n-th wave from a rising waveform illustrated in FIG. 3. According to the present exemplary embodiment, a transmittance value is calculated based on the peak value of the fourth wave (value indicated by a circle "○" illustrated in FIG. 3). Further, a peak value (P0 illustrated in FIG. 3) in a case where the recording material P is not present between the ultrasonic wave transmission unit 40a and the ultrasonic wave reception unit 40b and a peak value (P1 illustrated in FIG. 3) in a case where the recording material P is present therebetween are acquired. Then, a ratio of the peak value P1 to the peak value P0 (i.e., P1/P0) is calculated to determine the grammage. An analog-to-digital (A-D) conversion unit 512 can convert an analog signal generated by the detection circuit 511 into a digital signal. The converted signal can be stored in a reception waveform memory 513. The reception waveform memory 513 stores a reception waveform in a predetermined time since the drive start timing of the ultrasonic wave transmission unit 40a according to a counter value of the timer 516.

Next, a peak value extraction timing calculation operation is described below. In the present exemplary embodiment, the transmittance is determined using the peak value of the fourth wave output from the ultrasonic wave transmission unit 40a. An example operation for calculating the peak timing of the fourth wave is described in detail below. In the present exemplary embodiment, an example detection method is described below to identify a place of the wave corresponding to the peak value in an order of appearance of waves based on a time difference of the peaks that is caused in response to a change from 40 kHz to 45 kHz in frequency.

Figure 4A:
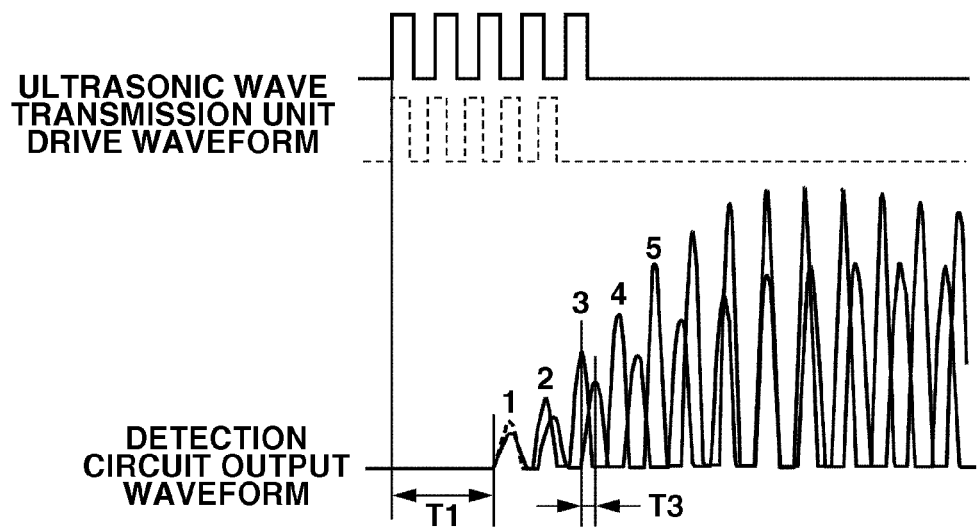
FIGS. 4A and 4B illustrate output waveforms obtainable when an environment temperature is changed.
Figure 4B:
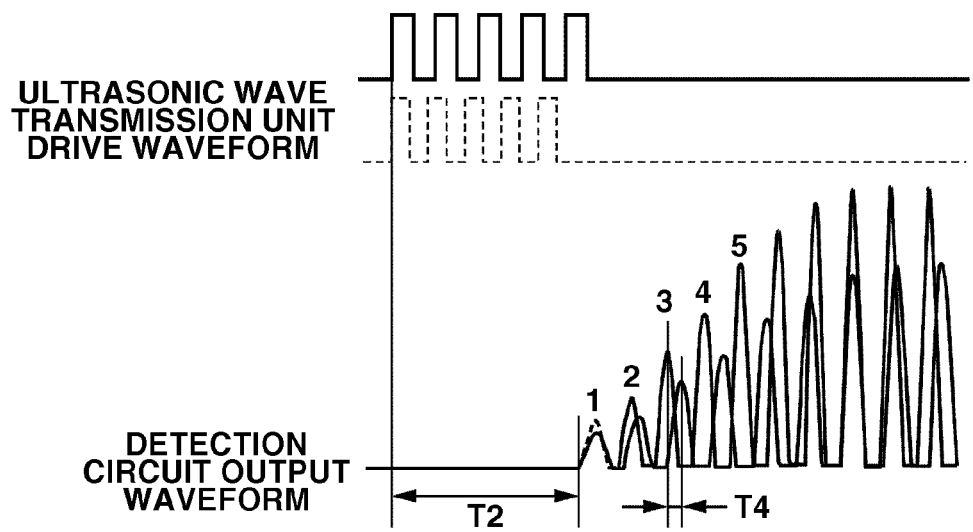

FIG. 4A illustrates an output waveform of the detection circuit 511 when the temperature is high. FIG. 4B illustrates an output waveform of the detection circuit 511 when the temperature is low. In FIGS. 4A and 4B, solid lines represent the waveforms obtained when the ultrasonic wave transmission unit is driven at the 40 kHz frequency, and dotted lines represent the waveforms obtained when the ultrasonic wave transmission unit is driven at the 45 kHz frequency. As illustrated in FIGS. 4A and 4B, time (T1, T2) from when driving of the ultrasonic wave transmission unit 40a is started to when the first wave is detected by the ultrasonic wave reception unit 40b is variable depending on the temperature. However, peak shift time T3 of the third wave in FIG. 4A is similar to peak shift time T4 of the third wave in FIG. 4B. In other words, it is understood that the shift time of the peak of the n-th wave is constant regardless of the frequency.

Next, a control sequence for calculating a peak of the fourth wave according to the present exemplary embodiment is described below with reference to a flowchart illustrated in FIG. 5. In step S101, the control unit 10 transmits rectangular waves of frequency 40 kHz/Duty 50% to the transmission control unit 50 for a time interval of 125 μsec. In step S102, the control unit 10 stores a reception waveform received by the ultrasonic wave reception unit 40b in the reception waveform memory 513.

In step S103, the control unit 10 transmits rectangular waves of frequency 45 kHz/Duty 50% to the transmission control unit 50 for a time interval of 111 μsec. In step S104, the control unit 10 stores a reception waveform received by the ultrasonic wave reception unit 40b in the reception waveform memory 513.

Figure 6A:
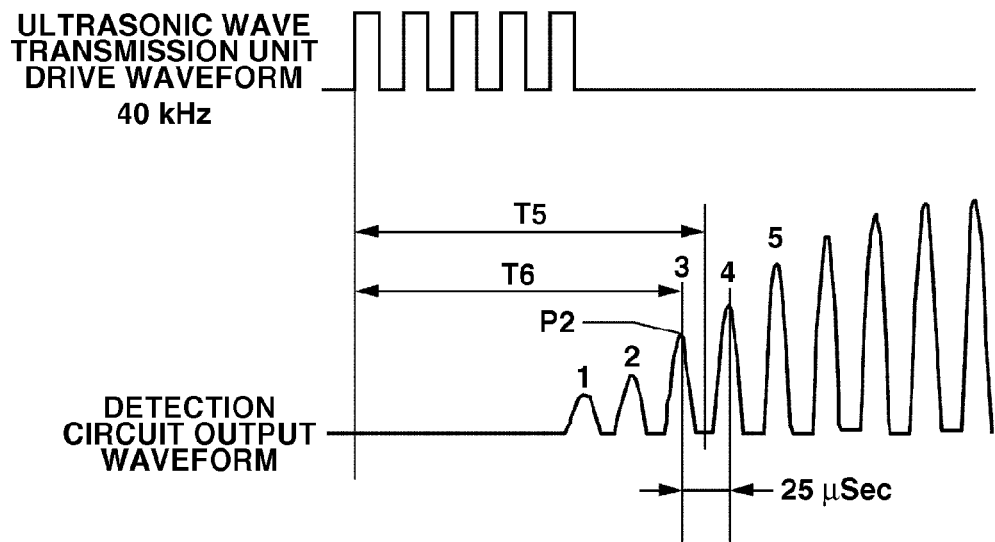
FIGS. 6A and 6B illustrate frequency changes in a waveform received when ultrasonic waves are transmitted at the 40 kHz frequency and in an output waveform received when ultrasonic waves are transmitted at the 45 kHz frequency according to the first exemplary embodiment.
Figure 6B:
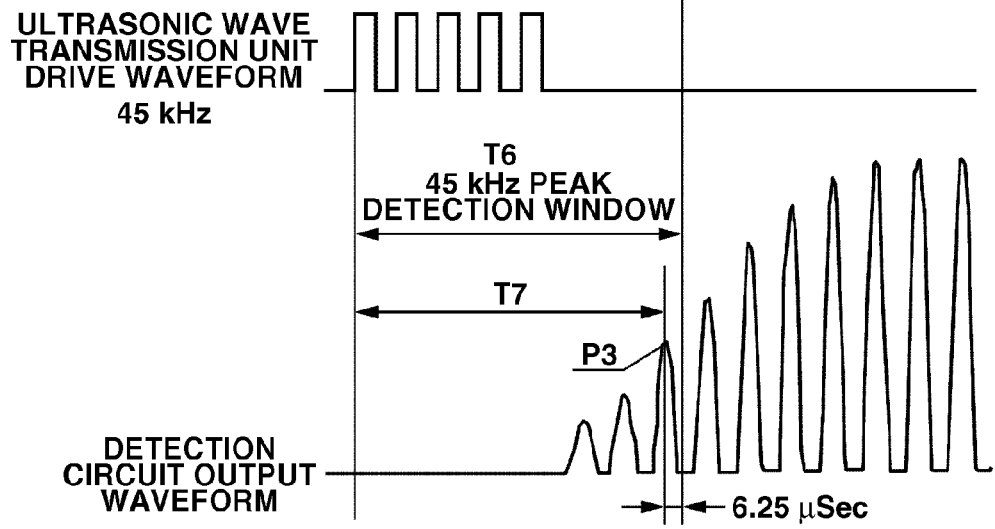

FIG. 6A illustrates a waveform received when ultrasonic waves are transmitted at the 40 kHz frequency. FIG. 6B illustrates a waveform received when ultrasonic waves are transmitted at the 45 kHz frequency. The processing to be performed in step S105 and the following steps is described with reference to FIGS. 6A and 6B. In step S105, the control unit 10 calculates a peak (P2 illustrated in FIG. 6A) of the wave that has lastly reached the ultrasonic wave reception unit 40b in a predetermined time interval T5 since the ultrasonic wave transmission unit 40a has started its driving operation, when the ultrasonic wave transmission unit 40a is driven at the 40 kHz frequency.

In step S106, the control unit 10 calculates a time interval T6 that is required for the peak P2 to reach the ultrasonic wave reception unit 40b since the drive start timing of the ultrasonic wave transmission unit 40a. In step S107, the control unit 10 calculates a peak (P3 illustrated in FIG. 6A) of the wave that has lastly reached the ultrasonic wave reception unit 40b in the time interval T6 when the ultrasonic wave transmission unit 40a is driven at the 45 kHz frequency. In the present exemplary embodiment, the time interval T6 between the drive start timing of the ultrasonic wave transmission unit 40a and the detection timing of the peak P2 is defined as a "45 kHz peak detection window."

In step S108, the control unit 10 calculates a time interval T7 that is required for the peak P3 to reach the ultrasonic wave reception unit 40b since the drive start timing of the ultrasonic wave transmission unit 40a. In step S109, the control unit 10 calculates a difference (T6−T7) that represents the shift time of the peak value (i.e., 6.25 μsec in FIG. 6B). In the present exemplary embodiment, the method for calculating the peak of the lastly reached wave in the predetermined time interval T5 since the drive start timing of the ultrasonic wave transmission unit 40a is described an example, although the method according to the present exemplary embodiment is not limited to the above-described example. For example, it is feasible to calculate a peak of the wave that appears firstly after the elapse of the time interval T5 and calculate the shift time of the peak value according to a method similar to the above-described method.

In step S110, the control unit 10 compares the shift time of the peak value obtained in step S109 with data of Table 1 stored in the peak calculation unit 515, and identifies the place of the detected wave in the appearance order of waves. In the present exemplary embodiment, it is understood that the peak value corresponds to the third wave because the shift time is 6.25 μsec.

In step S111, the control unit 10 acquires a time difference (25 μsec) relative to the peak value of the fourth wave, as a peak value of the m-th wave, with reference to the peak value of the third wave obtained from Table 1. In step S112, the control unit 10 reads the peak value of the fourth wave from the waveform stored in the reception waveform memory 513 when the frequency is 40 kHz.

In step S113, the control unit 10 stores the read peak value of the fourth wave in a storage unit 101. As described above, the ultrasonic wave detection apparatus according to the present exemplary embodiment can calculate the place of the wave corresponding to the peak value in the appearance order of waves with reference to the time difference in peak value between two different frequencies without any influence (e.g., environment). Further, a peak value of a predetermined wave number can be acquired based on the calculated peak value.

TABLE 1

| n-th wave | shift time | time difference relative to peak of fourth wave |
|---|---|---|
| 2nd wave | 3.47 μSec | 50 μSec |
| 3rd wave | 6.25 μSec | 25 μSec |
| 4th wave | 9.03 μSec | 0 μSec |
| 5th wave | 11.81 μSec | −25 μSec |
| 6th wave | 14.58 μSec | −50 μSec |
| 7th wave | 17.36 μSec | −75 μSec |

Figure 7A:
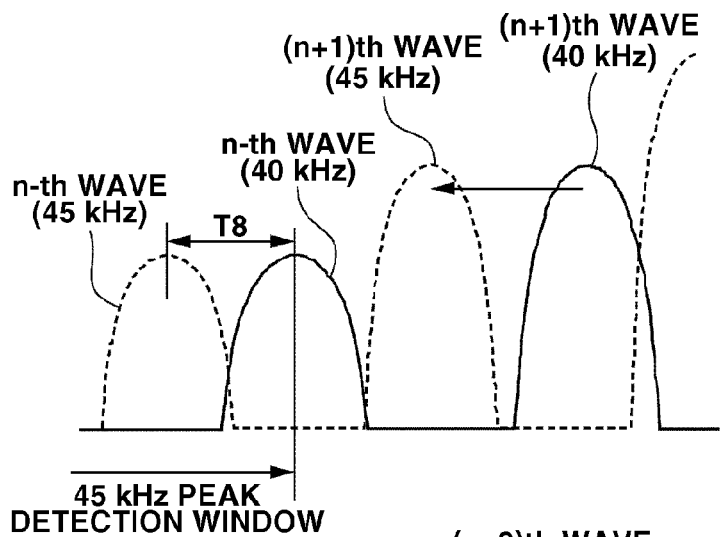
FIGS. 7A to 7C illustrate waves usable to detect a shift time of the peak according to the first exemplary embodiment.
Figure 7B:
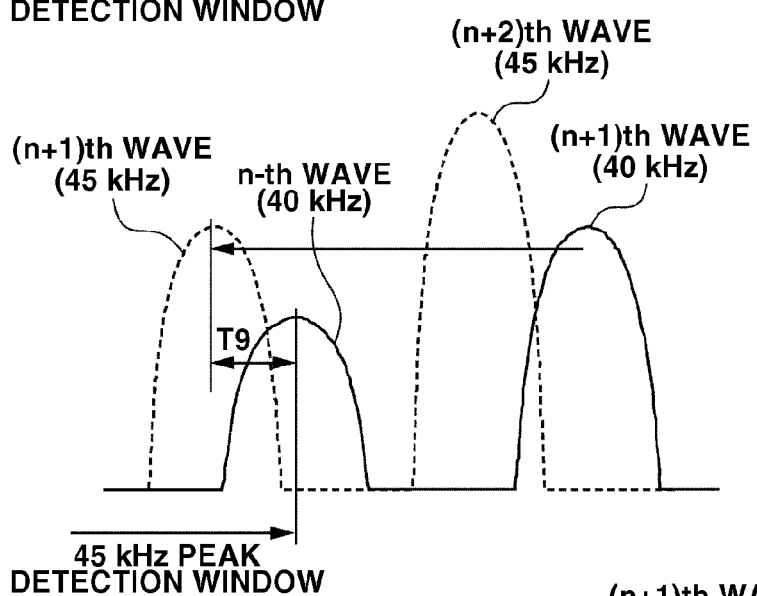
Figure 7C:
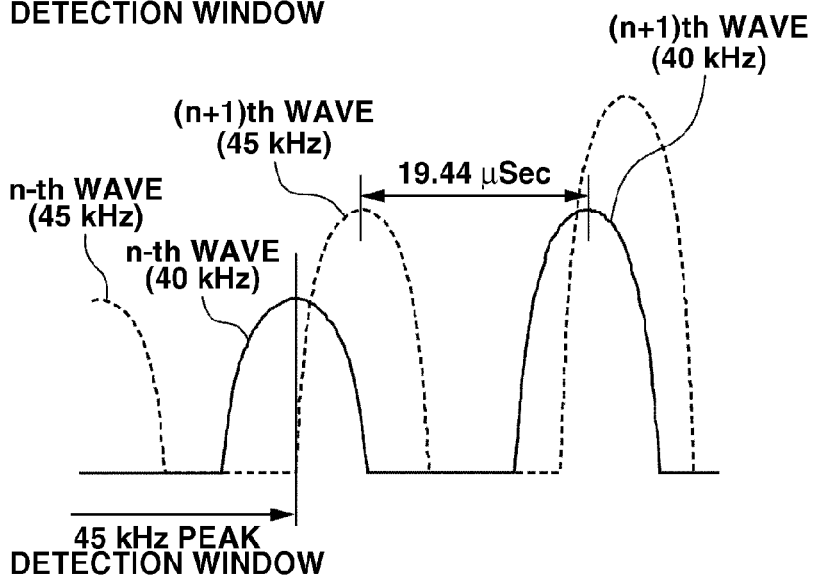

In the present exemplary embodiment, the time interval T5 illustrated in FIG. 6A is set in such a way as to surely detect respective peaks of the first to seventh waves even when the environment (e.g., temperature or humidity) is variable. The setting reason of the time interval T5 is described below with reference to output waveforms obtainable when the ultrasonic wave transmission unit 40a is driven at the 40 kHz frequency and output waveforms obtainable when the ultrasonic wave transmission unit 40a is driven at the 45 kHz frequency as illustrated in FIGS. 7A to 7C. In FIGS. 7A to 7C, the solid lines indicate the output waveforms of 40 kHz ultrasonic waves, and the dotted lines indicate the output waveforms of 45 kHz ultrasonic waves.

FIG. 7A indicates a state where a peak of the n-th wave is present in the "45 kHz peak detection window" when the ultrasonic wave transmission unit 40a is driven at the 45 kHz frequency. In this state, the time difference calculation unit 514 can calculate a time difference (T8) in the peak value of the same n-th wave of the output waveform between the 40 kHz driving operation and the 45 kHz driving operation.

FIG. 7B indicates a state where a peak of the (n+1)-th wave is present in the "45 kHz peak detection window" when the ultrasonic wave transmission unit 40a is driven at the 45 kHz frequency. In this state, the time difference calculation unit 514 calculates a time difference (T9) between the peak value of the n-th wave of the output waveform in the 40 kHz driving operation and the peak value of the (n+1)-th wave of the output waveform in the 45 kHz driving operation. Thus, the time difference calculation unit 514 fails in detection because the time difference calculation unit 514 cannot compare the peak values of the same wave number.

Hence, according to the present exemplary embodiment, the shift time of the peak is set to be equal to or less than 19.44 μsec so that the (n+1)-th wave in the 45 kHz driving operation can be excluded from the "45 kHz peak detection window" as illustrated in FIG. 7C. When the shift time of the peak of each wave number is checked, the shift time of the peak of the eighth wave is 20.14 μsec. In other words, the eighth wave cannot be detected because the above-described condition "equal to or less than 19.44 μsec" cannot be satisfied. Accordingly, using the first to seventh waves in detecting the shift time of the peak is useful to eliminate an error detection that may occur when the peak of the n-th wave is compared with the peak of the (n+1)-th wave.

Figure 8:
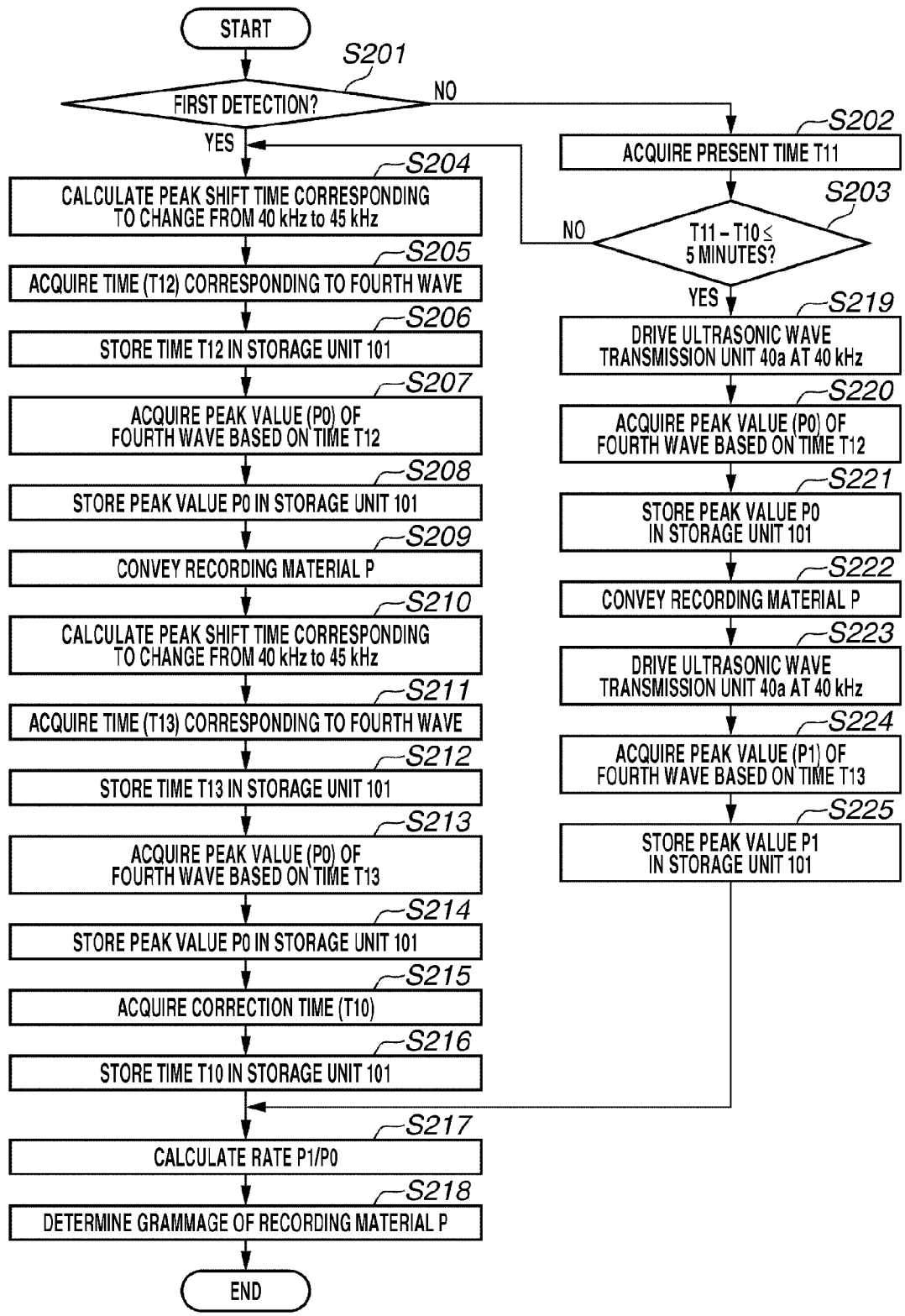
FIG. 8 is a flowchart illustrating detection control using ultrasonic waves according to the first exemplary embodiment.

FIG. 8 is a flowchart illustrating detection control using ultrasonic waves according to the present exemplary embodiment. An example of the control described with reference to FIG. 8 is control for detecting the above-described peak of the fourth wave in a predetermined time interval. In step S201, the control unit 10 determines whether the present detection is the first detection after the power source is turned on. If it is determined that the present detection is not the first detection (NO in step S201), then in step S202, the control unit 10 acquires the present time (T11).

Next, in step S203, the control unit 10 determines whether a difference between the fourth-wave peak detection time (T10) and the present time (T11) is equal to or less than five minutes. The determination condition in step S203 is not limited to the above-described example (i.e., five minutes). For example, an appropriate value can be set according to a user setting. If it is determined that the time difference is greater than five minutes (NO in step S203), the control unit 10 performs control to detect a peak position of the fourth wave in step S204 and subsequent steps.

In step S204, the control unit 10 calculates the shift time of the peak when the driving frequency of the ultrasonic wave transmission unit 40a is changed from 40 kHz to 45 kHz in the state where the recording material P is not present. In step S205, the control unit 10 detects a time interval (T12) between the drive start timing and the fourth-wave peak detection timing, when the frequency is 40 kHz, based on the shift time of the peak obtained in step S204.

In step S206, the control unit 10 stores the detected time interval T12 in the storage unit 101. In step S207, the control unit 10 extracts the peak value (P0) of the fourth wave from the reception waveform acquired at the 40 kHz frequency, with reference to the time interval T12. In step S208, the control unit 10 stores the detected peak value P0 in the storage unit 101.

In step S209, the control unit 10 causes the paper feeding roller 23 to convey the recording material P to a space between the ultrasonic wave transmission unit 40a and the ultrasonic wave reception unit 40b. In step S210, the control unit 10 changes the driving frequency of the ultrasonic wave transmission unit 40a from 40 kHz to 45 kHz in the state where the recording material P is present, and calculates the shift time of the peak. In step S211, the control unit 10 detects a time interval (T13) between the drive start timing and the fourth-wave peak detection timing when the frequency is 40 kHz, based on the shift time of the peak obtained in step S210.

In step S212, the control unit 10 stores the detected time interval T13 in the storage unit 101. In step S213, the control unit 10 extracts a peak value (P1) of the fourth wave from the reception waveform acquired at the 40 kHz frequency, with reference to the time interval T13. In step S214, the control unit 10 stores the detected peak value P1 in the storage unit 101. In step S215, the control unit 10 calculates a correction time (T10). In step S216, the control unit 10 stores the correction time (T10) in the storage unit 101.

Figure 9:
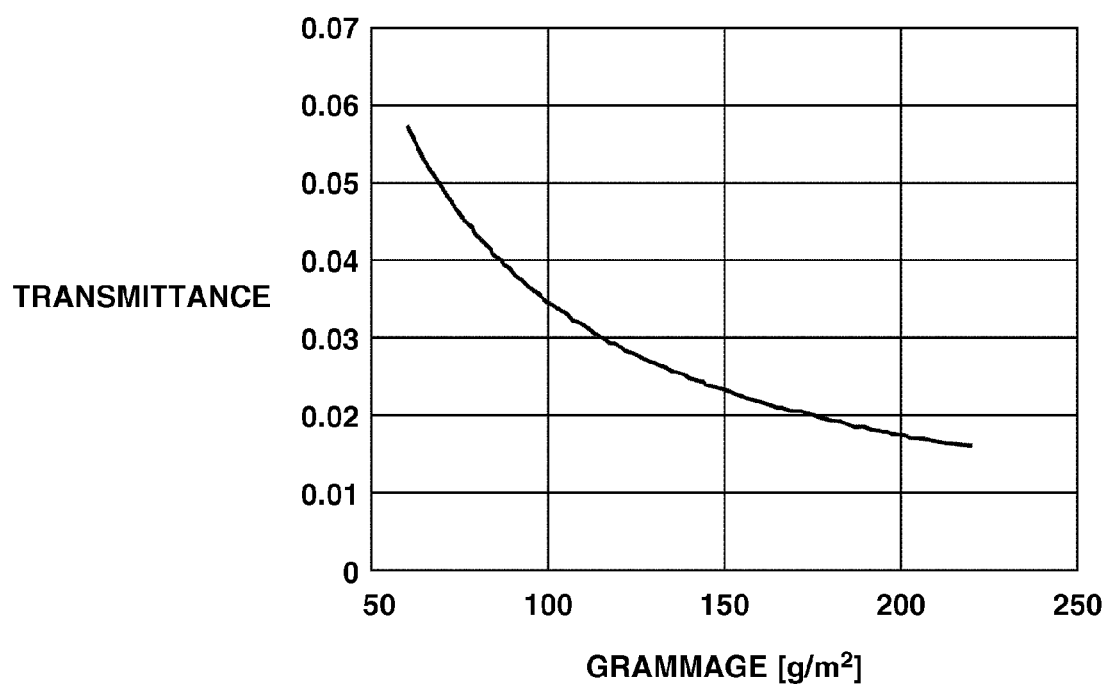
FIG. 9 is a graph illustrating a relationship between grammage and transmittance.

In step S217, the control unit 10 calculates the rate P1/P0 and stores the calculation result in the storage unit 101. In step S218, the control unit 10 determines the grammage of the recording material P based on the calculated rate P1/P0 with reference to a graph illustrating a relationship between the grammage and the transmittance in FIG. 9. The graph in FIG. 9 illustrates an example of a relationship between an output value of the ultrasonic wave and the grammage of the recording material P. For example, if the detected transmittance value is lower than that of a single recording material P, it can be determined that the recording material P is in the double feed state.

If it is determined that the present detection is not the first detection (NO in step S201) and it is determined that the time difference is equal to or less than five minutes (YES in step S203), the control unit 10 performs control processing in step S219 and subsequent steps. In step S219, the control unit 10 drives the ultrasonic wave transmission unit 40a at the 40 kHz frequency in the state where the recording material P is not present. In step S220, the control unit 10 detects the peak value (P0) of the fourth wave with reference to the time interval (T12) between the drive start timing and the fourth-wave peak detection timing stored in step S206. In step S221, the control unit 10 stores the detected peak value (P0) in the storage unit 101.

In step S222, the control unit 10 causes the paper feeding roller to convey the recording material P to the space between the ultrasonic wave transmission unit 40a and the ultrasonic wave reception unit 40b. In step S223, the control unit 10 drives the ultrasonic wave transmission unit 40a at the 40 kHz frequency in the state where the recording material P is present. In step S224, the control unit 10 detects the peak value (P1) of the fourth wave with reference to the time interval (T13) between the drive start timing and the fourth-wave peak detection timing stored in step S212.

In step S225, the control unit 10 stores the peak value (P1) of the fourth wave in the storage unit 101. In step S217, the control unit 10 calculates the rate P1/P0 and stores the calculation result in the storage unit 101. In step S218, the control unit 10 determines the grammage of the recording material P based on the calculated rate P1/P0 with reference to the graph illustrating the relationship between the grammage and the transmittance in FIG. 9.

As described above, the detection method according to the present exemplary embodiment can identify the place of the detected wave in appearance order of waves transmitted from the ultrasonic wave transmission unit based on the shift time of the peaks between reception waves generated when the ultrasonic wave transmission unit is driven at different frequencies. Accordingly, the detection method according to the present exemplary embodiment can accurately calculate the detection timing of the predetermined n-th wave. Therefore, the detection method according to the present exemplary embodiment enables the ultrasonic wave detection apparatus to accurately obtain the detection timing of the reception signal and accurately perform the grammage detection without performing any correction according to the environment. Further, because no correction according to the environment is performed, the detection method according to the present exemplary embodiment can reduce the load of the control unit 10. Furthermore, because no correcting operation is performed as a preparation operation, the time required for the correction operation can be reduced in the entire detection time.

According to the peak detection method described in the first exemplary embodiment, the driving frequency of the ultrasonic wave transmission unit 40a is changed from 40 kHz to 45 kHz. A peak detection method according to a second exemplary embodiment is different from the method described in the first exemplary embodiment in that the driving frequency of the ultrasonic wave transmission unit is changed from 45 kHz to 40 kHz. Descriptions of the configuration similar to that described in the first exemplary embodiment are not repeated.

Figure 10:
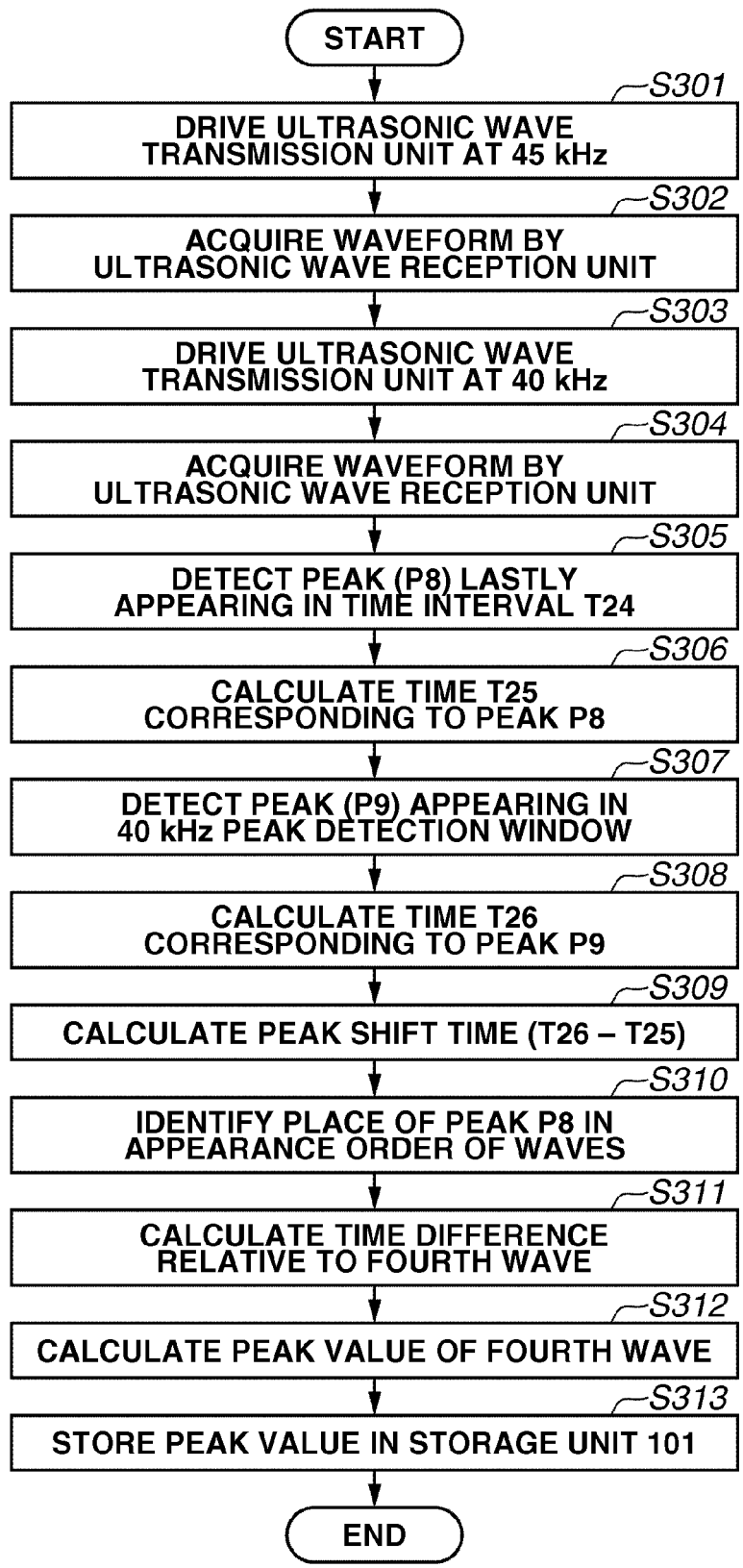
FIG. 10 is a flowchart illustrating a control sequence for calculating a peak of the fourth wave according to a second exemplary embodiment of the present invention.

FIG. 10 is a flowchart illustrating a control sequence for calculating a peak of the fourth wave according to the present exemplary embodiment. In step S301, the control unit 10 transmits rectangular waves of frequency 45 kHz/Duty 50% to the transmission control unit 50 for a time interval of 111 μsec. In step S302, the control unit 10 stores a reception waveform received by the ultrasonic wave reception unit 40b in the reception waveform memory 513. In step S303, the control unit 10 transmits rectangular waves of frequency 40 kHz/Duty 50% to the transmission control unit 50 for a time interval of 125 μsec. In step S304, the control unit 10 stores a reception waveform received by the ultrasonic wave reception unit 40b in the reception waveform memory 513.

Figure 11A:
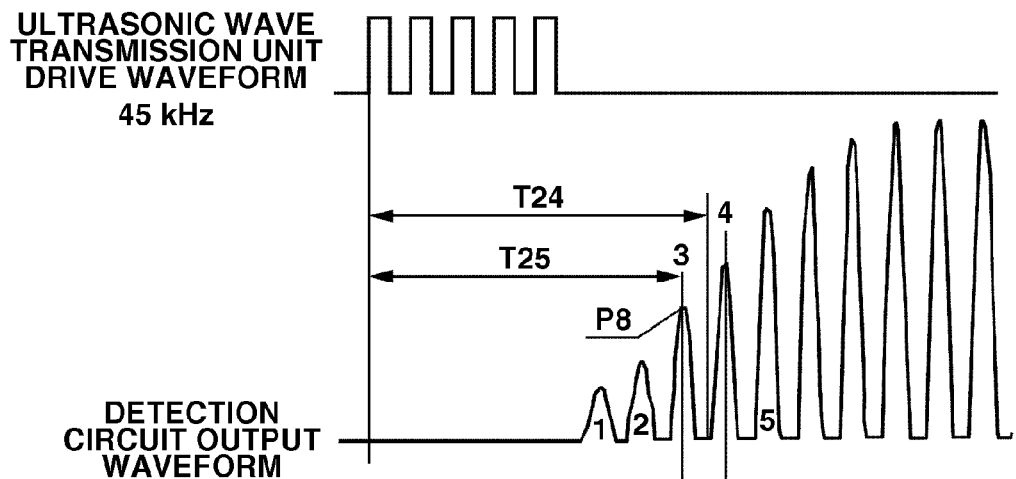
FIGS. 11A and 11B illustrate frequency changes in a waveform received when ultrasonic waves are transmitted at the 40 kHz frequency and in an output waveform received when ultrasonic waves are transmitted at the 45 kHz frequency according to the second exemplary embodiment.
Figure 11B:
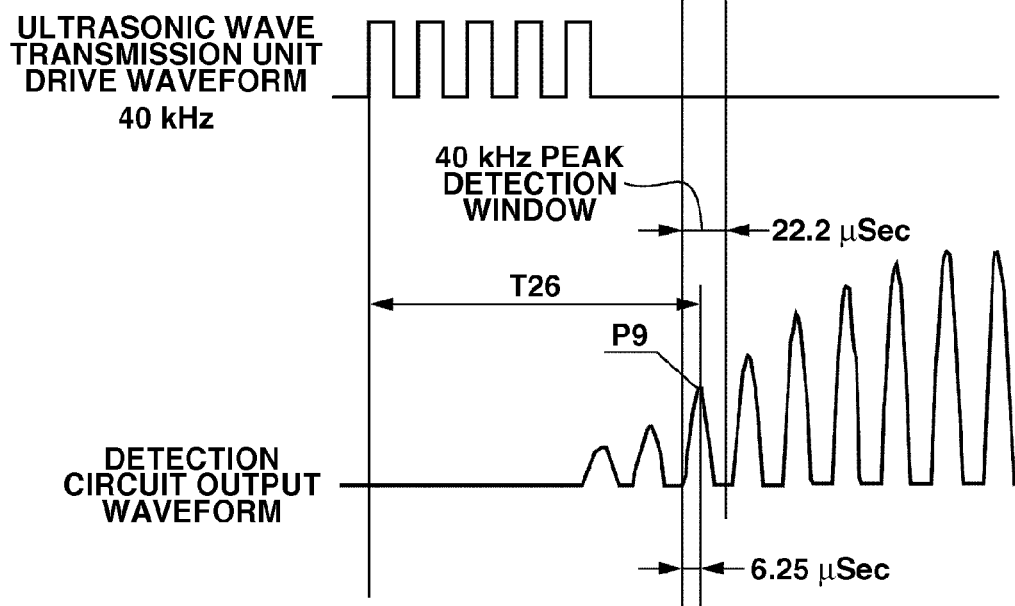

In the processing in steps S305 through S309, the control unit 10 controls the time difference calculation unit 514 to calculate the shift time of the peak. The control processing is described below with reference to FIGS. 11A and 11B. FIG. 11A illustrates waveform data stored when the ultrasonic wave transmission unit 40a is driven at the 45 kHz frequency. FIG. 11B illustrates waveform data stored when the ultrasonic wave transmission unit 40a is driven at the 40 kHz frequency.

In step S305, the control unit 10 calculates a peak (P8 illustrated in FIG. 11A) of the wave that has lastly reached the ultrasonic wave reception unit 40b in a time interval T24 since the drive start timing when the ultrasonic wave transmission unit 40a is driven at the 45 kHz frequency. In step S306, the control unit 10 calculates a time interval (T25) that is required for the peak P8 to reach the ultrasonic wave reception unit 40b since the drive start timing. In step S307, the control unit 10 detects a peak (P9 illustrated in FIG. 11B) that is present in a "40 kHz peak detection window" illustrated in FIG. 11B.

In step S308, the control unit 10 calculates a time interval (T26) that is required for the peak P9 to reach the ultrasonic wave reception unit 40b since the drive start timing. In step S309, the control unit 10 calculates a time difference (T26–T25) that represents the shift time of the peak (i.e., 6.25 μsec in FIG. 11B). In the present exemplary embodiment, the method for calculating the peak of the lastly reached wave in the predetermined time interval T24 since the drive start timing of the ultrasonic wave transmission unit 40a is described an example, although the method according to the present exemplary embodiment is not limited to the above-described example. For example, it is feasible to calculate a peak of the wave that appears firstly after the elapse of the time interval T24 and calculate the shift time of the peak value according to a method similar to the above-described method.

In step S310, the control unit 10 determines that the detected wave is the third wave based on the data of Table 2 stored in the peak calculation unit 515 and the shift time of the peak calculated in step S309. In step S311, the control unit 10 calculates a time difference (22.2 μsec) relative to the peak position of the fourth wave with reference to Table 2. In step S312, the control unit 10 calculates a peak value of the fourth wave with reference to the calculated time difference, from the waveform stored in the reception waveform memory 513 when the driving frequency is 40 kHz. In step S313, the control unit 10 stores the calculated peak value of the fourth wave in the storage unit 101.

TABLE 2

| n-th wave | shift time | time difference relative to peak of fourth wave |
|---|---|---|
| 2nd wave | 3.47 μSec | 44.4 μSec |
| 3rd wave | 6.25 μSec | 22.2 μSec |
| 4th wave | 9.03 μSec | 0.0 μSec |
| 5th wave | 11.81 μSec | −22.2 μSec |
| 6th wave | 14.58 μSec | −44.4 μSec |

Figure 12A:
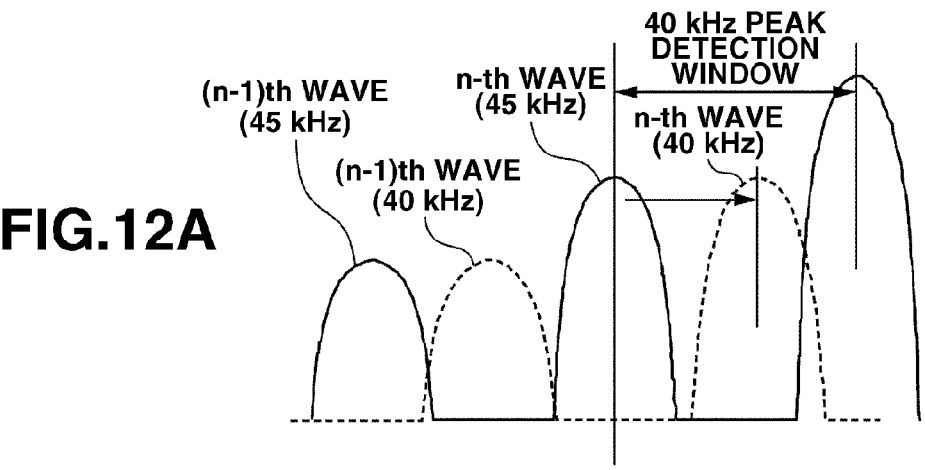
FIGS. 12A to 12C illustrate waves usable to detect a shift time of the peak according to the second exemplary embodiment.
Figure 12B:
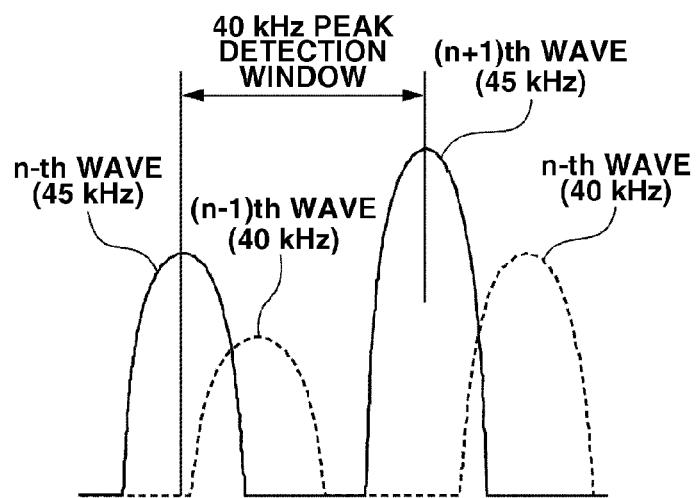
Figure 12C:
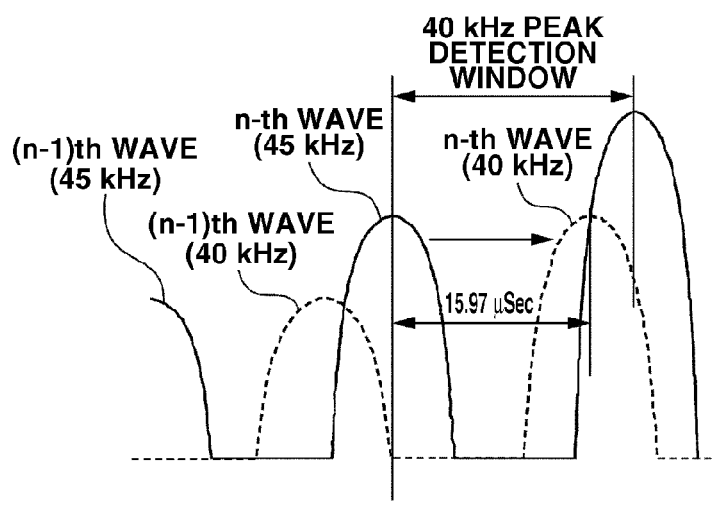

In the present exemplary embodiment, setting of the time interval T24 illustrated in FIG. 11A is performed in such a way as to surely detect respective peaks of the first to seventh waves even when the environment (e.g., temperature or humidity) is variable. The setting reason of the time interval T24 is described below with reference to output waveforms obtainable when the ultrasonic wave transmission unit 40a is driven at the 45 kHz frequency and output waveforms obtainable when the ultrasonic wave transmission unit 40a is driven at the 40 kHz frequency as illustrated in FIGS. 12A to 12C. In FIGS. 12A to 12C, the solid lines indicate the output waveforms of 45 kHz ultrasonic waves, and the dotted lines indicate the output waveforms of 40 kHz ultrasonic waves.

FIG. 12A indicates a state where a peak of the n-th wave is present in the "40 kHz peak detection window" when the ultrasonic wave transmission unit 40a is driven at the 40 kHz frequency. In this state, the time difference calculation unit 514 can calculate a time difference (T27) in the peak value of the same n-th wave of the output waveform between the 45 kHz driving operation and the 40 kHz driving operation.

FIG. 12B indicates a state where a peak of the (n−1)-th wave is present in the "40 kHz peak detection window" when the ultrasonic wave transmission unit 40a is driven at the 40 kHz frequency. In this state, the time difference calculation unit 514 calculates a time difference (T28) between the peak value of the n-th wave of the output waveform in the 45 kHz driving operation and the peak value of the (n−1)-th wave of the output waveform in the 40 kHz driving operation. Thus, the time difference calculation unit 514 fails in detection because the time difference calculation unit 514 cannot compare the peak values of the same wave number.

Hence, according to the present exemplary embodiment, the shift time of the peak is set to be equal to or less than 15.97 μsec so that the (n−1)-th wave in the 40 kHz driving operation can be excluded from the "40 kHz peak detection window", as illustrated in FIG. 12C. When the shift time of the peak of each wave number is checked, the peak shift time of the seventh wave is 17.36 μsec. In other words, the seventh wave cannot be detected because the above-described condition "equal to or less than 15.97 μsec" cannot be satisfied. Accordingly, using the first to sixth waves in detecting the shift time of the peak is useful to eliminate an error detection that may occur when the peak of the n-th wave is compared with the peak of the (n−1)-th wave.

As described above, even when the ultrasonic wave transmission unit is driven at the frequency lower than the reference frequency, which is opposite to the driving frequency described in the first exemplary embodiment, the detection method according to the present exemplary embodiment can identify the place of the detected wave in appearance order of waves transmitted from the ultrasonic wave transmission unit based on the shift time of the peaks between generated reception waves. Accordingly, the detection method according to the present exemplary embodiment can accurately calculate the detection timing of the predetermined n-th wave. Therefore, the detection method according to the present exemplary embodiment enables the ultrasonic wave detection apparatus to accurately obtain the detection timing of the reception signal and accurately perform the grammage detection without performing any correction according to the environment. Further, because no correction according to the environment is performed, the detection method according to the present exemplary embodiment can reduce the load of the control unit 10. Furthermore, because no correcting operation is performed as a preparation operation, the time required for the correction operation can be reduced in the entire detection time.

According to the peak detection method described in the first exemplary embodiment, the driving frequency of the ultrasonic wave transmission unit 40a is changed from 40 kHz to 45 kHz. A peak detection method according to a third exemplary embodiment is different from the method described in the first exemplary embodiment in that the driving frequency of the ultrasonic wave transmission unit 40a is changed from 30 kHz to 50 kHz to make a difference between the two frequencies larger. Descriptions of the configuration similar to that described in the first and second exemplary embodiments are not repeated.

Figure 13:
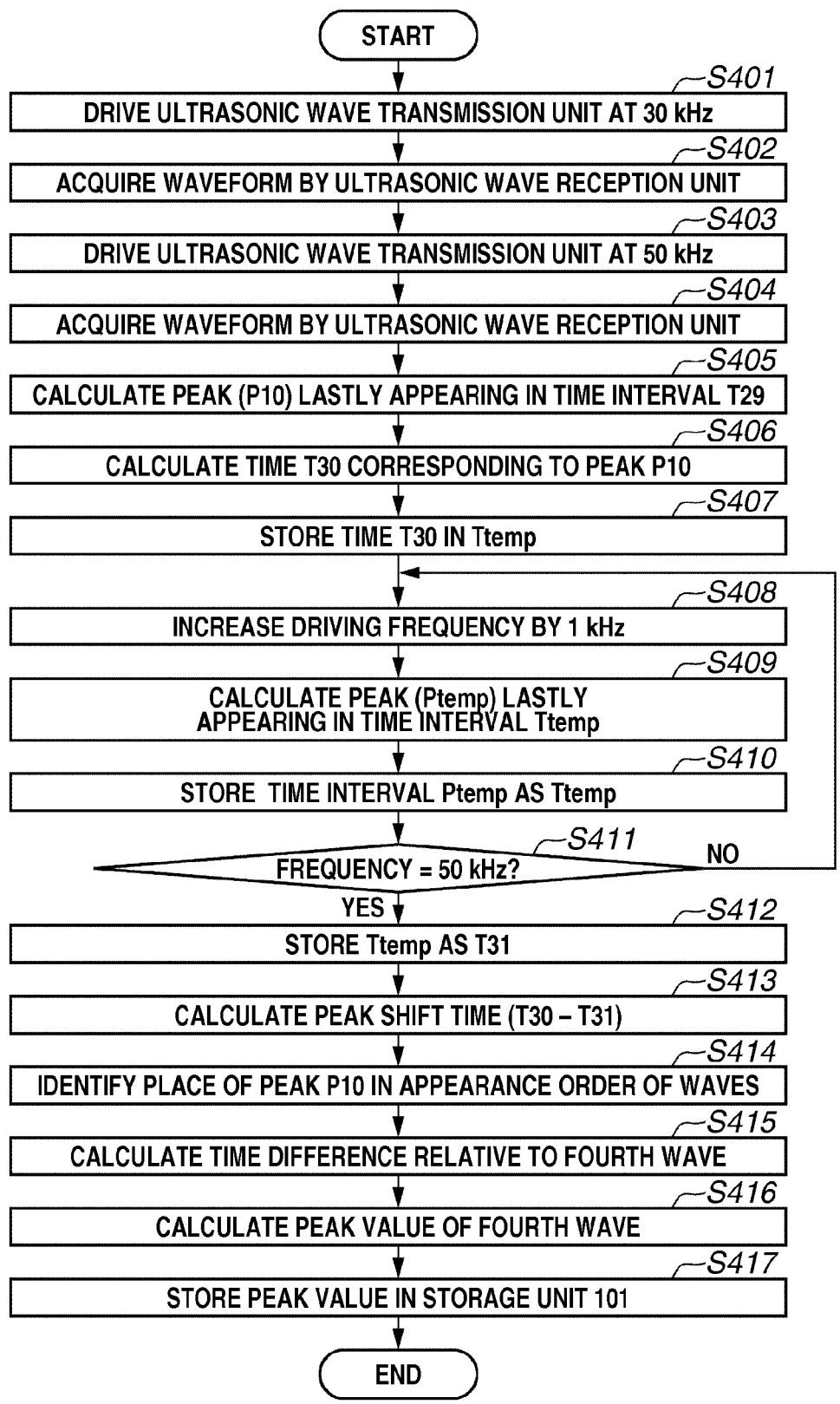
FIG. 13 is a flowchart illustrating a control sequence for calculating a peak of the fourth wave according to a third exemplary embodiment of the present invention.

FIG. 13 is a flowchart illustrating a control sequence for calculating a peak of the fourth wave according to the present exemplary embodiment. In step S401, the control unit 10 transmits rectangular waves of frequency 30 kHz/Duty 50% to the transmission control unit 50 for a time interval of 166 μsec. In step S402, the control unit 10 stores a reception waveform received by the ultrasonic wave reception unit 40b in the reception waveform memory 513. In step S403, the control unit 10 transmits rectangular waves of frequency 50 kHz/Duty 50% to the transmission control unit 50 for a time interval of 100 μsec. In step S404, the control unit 10 stores a reception waveform received by the ultrasonic wave reception unit 40b in the reception waveform memory 513.

Figure 14A:
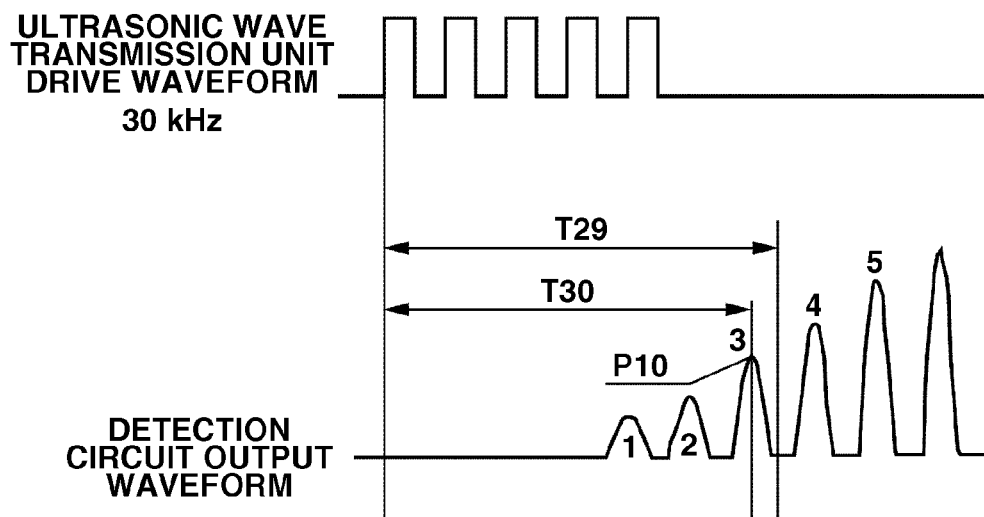
FIGS. 14A and 14B illustrate frequency changes in a waveform received when ultrasonic waves are transmitted at the 30 kHz frequency and in an output waveform received when ultrasonic waves are transmitted at the 50 kHz frequency according to the third exemplary embodiment.
Figure 14B:
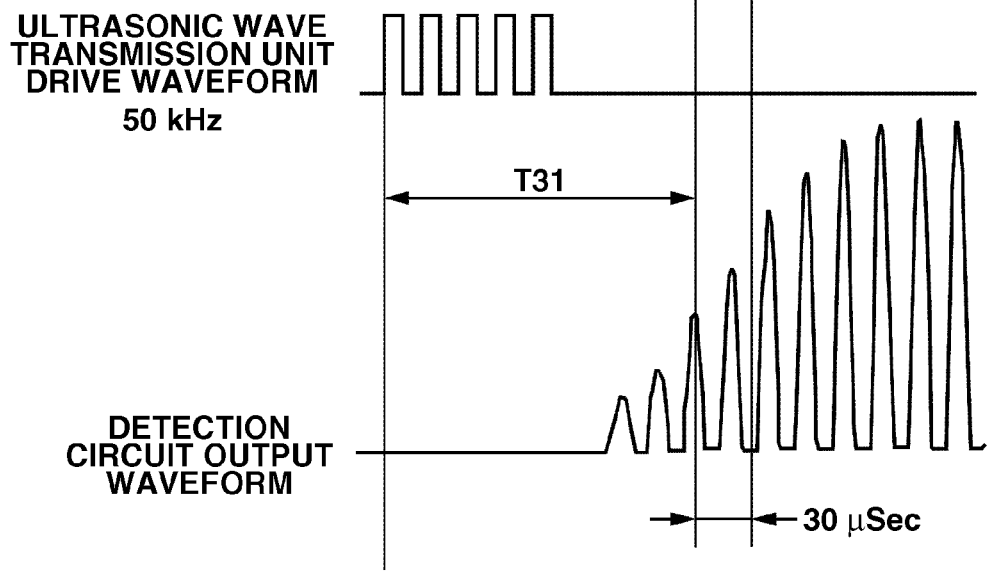

In the processing in steps S405 through S409, the control unit 10 controls the time difference calculation unit 514 to calculate the shift time of the peak. The control processing is described below with reference to FIGS. 14A and 14B. FIG. 14A illustrates waveform data stored when the ultrasonic wave transmission unit 40a is driven at the frequency of 30 kHz. FIG. 14B illustrates waveform data stored when the ultrasonic wave transmission unit 40a is driven at the frequency of 50 kHz.

In step S405, the control unit 10 calculates a peak (P10 illustrated in FIG. 14A) of the wave that has lastly reached the ultrasonic wave reception unit 40b in a time interval T29 since the drive start timing when the ultrasonic wave transmission unit 40a is driven at the 30 kHz frequency. In step S406, the control unit 10 calculates a time interval (T30) that is required for the peak P10 to reach the ultrasonic wave reception unit 40b since the drive start timing. In the present exemplary embodiment, the method for calculating the peak of the lastly reached wave in the predetermined time interval T29 since the drive start timing of the ultrasonic wave transmission unit 40a is described an example, although the method according to the present exemplary embodiment is not limited to the above-described example. For example, it is feasible to calculate a peak of the wave that appears firstly after the elapse of the time interval T29 and calculate the shift time of the peak value according to a method similar to the above-described method.

The processing in steps S407 and the subsequent steps is control in which the driving frequency of the ultrasonic wave transmission unit 40a is changed stepwise from 30 kHz to 50 kHz by an increment of 1 kHz to detect the peak of the n-th wave, which is similar to the peak P10 detected at the 30 kHz frequency, at 50 kHz frequency. In step S407, the control unit 10 stores the detected value of the time interval T30 as "Ttemp." In step S408, the control unit 10 increases the driving frequency of the ultrasonic wave transmission unit 40a by 1 kHz from 30 kHz. In step S409, the control unit 10 detects a peak (Ptemp) that has lastly detected in the time interval Ttemp since the drive start timing of the ultrasonic wave transmission unit 40a. In step S410, the control unit 10 calculates a time interval between the drive start timing of the ultrasonic wave transmission unit 40a and the detected peak Ptemp, and stores the calculated time interval as an updated value of the time interval Ttemp.

In step S411, the control unit 10 determines whether the driving frequency of the ultrasonic wave transmission unit 40a has reached 50 kHz. If it is determined that the driving frequency of the ultrasonic wave transmission unit 40a has reached 50 kHz (YES in step S411), then in step S412, the control unit 10 stores the Ttemp value as a time interval T31 in the storage unit 101.

If it is determined that the driving frequency of the ultrasonic wave transmission unit 40a has not yet reached 50 kHz (NO in step S411), the operation returns to step S408 to repeat the above-described processing for the next driving frequency increased by 1 kHz until the driving frequency reaches 50 kHz.

In step S413, the control unit 10 calculates a time difference (T30−T31) that represents the shift time of the peak (30 μsec in FIG. 14B).

In step S414, the control unit 10 determines that the detected wave is the third wave based on the shift time of the peak obtained in step S413 with reference to Table 3 stored in the peak calculation unit 515. In step S415, the control unit 10 calculates a time difference (33.3 μsec) relative to the peak position of the fourth wave with reference to Table 3, in the kHz driving operation.

In step S416, the control unit 10 calculates a peak value of the fourth wave with reference to the calculated time difference, from the waveform stored in the reception waveform memory 513 when the driving frequency is 30 kHz. In step S417, the control unit 10 stores the calculated peak value of the fourth wave in the storage unit 101.

TABLE 3

| n-th wave | shift time | time difference relative to peak of fourth wave |
|---|---|---|
| 2nd wave | 16.7 μSec | 66.7 μSec |
| 3rd wave | 30.0 μSec | 33.3 μSec |
| 4th wave | 43.3 μSec | 0.0 μSec |
| 5th wave | 56.7 μSec | −33.3 μSec |
| 6th wave | 70.0 μSec | −66.7 μSec |
| 7th wave | 83.3 μSec | −100.0 μSec |
| 8th wave | 96.7 μSec | −133.3 μSec |

As described above, even when the frequency difference is increased compared to that described in the first exemplary embodiment, the detection method according to the present exemplary embodiment can identify the place of the detected wave in appearance order of waves transmitted from the ultrasonic wave transmission unit based on the shift time of the peaks between generated reception waves. Accordingly, the detection method according to the present exemplary embodiment can accurately calculate the detection timing of the predetermined n-th wave. Therefore, the detection method according to the present exemplary embodiment enables the ultrasonic wave detection apparatus to accurately obtain the detection timing of the reception signal and accurately perform the grammage detection without performing any correction according to the environment. Further, because no correction according to the environment is performed, the detection method according to the present exemplary embodiment can reduce the load of the control unit 10. Furthermore, because no correcting operation is performed as a preparation operation, the time required for the correction operation can be reduced in the entire detection time.

In addition, it is feasible to change the frequency from a higher level to a low level, as described in the second exemplary embodiment. More specifically, even when the driving frequency is changed from 50 kHz to 30 kHz, the detection method according to the present exemplary embodiment enables the ultrasonic wave detection apparatus to accurately obtain the detection timing of the reception signal and accurately perform the grammage detection without performing any correction according to the environment.

In the above-described first to third exemplary embodiments, the factor used in selecting a target wave from which the shift time of the peak is obtained is the "time." According to a fourth exemplary embodiment, a target wave is selected based on a "the number of times a detection signal exceeds a predetermined threshold value" instead of the "time". Descriptions of the configuration similar to that described in the first to third exemplary embodiments are not repeated.

Figure 15:
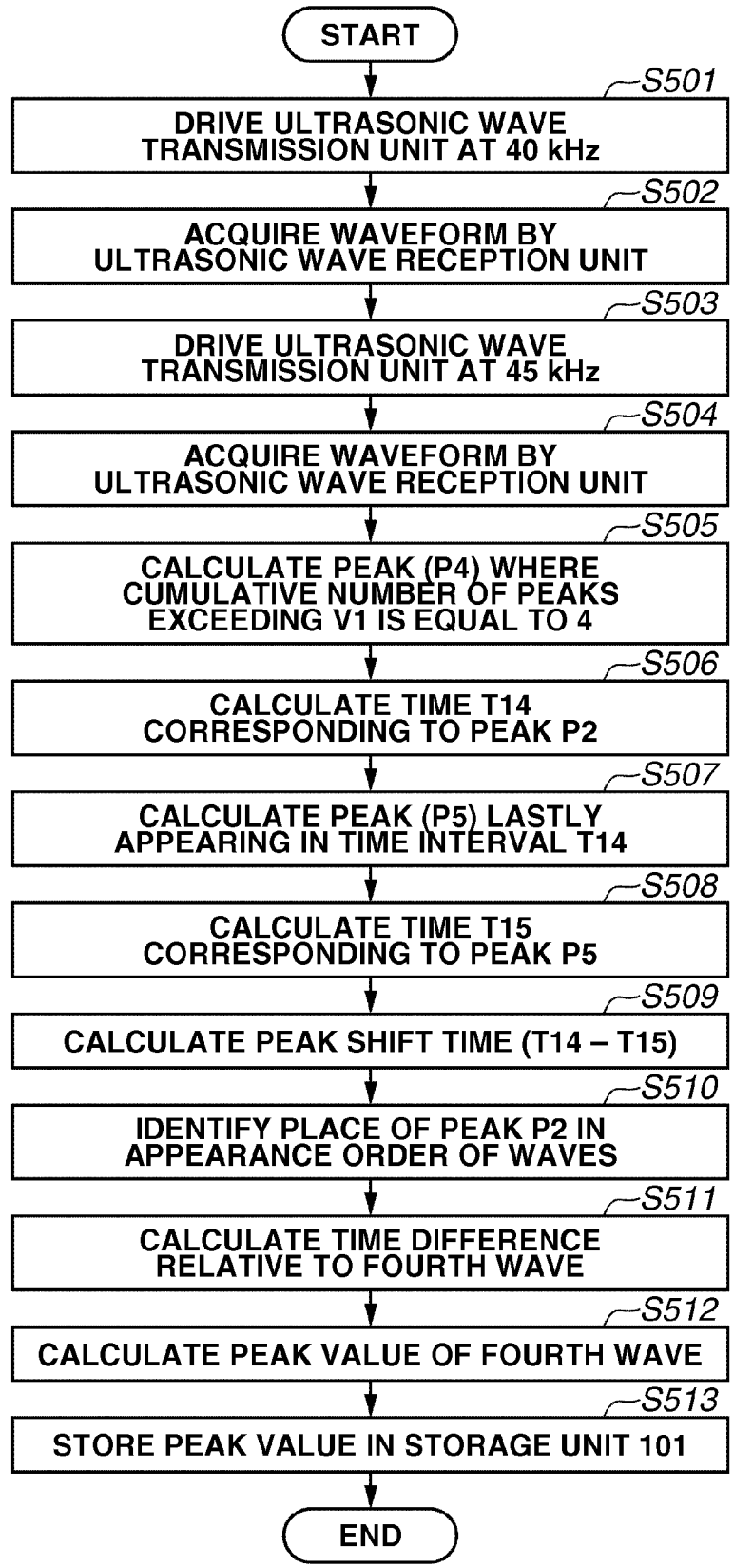
FIG. 15 is a flowchart illustrating a control sequence for calculating a peak of the fourth wave according to a fourth exemplary embodiment of the present invention.

FIG. 15 is a flowchart illustrating a control sequence for calculating a peak of the fourth wave according to the present exemplary embodiment. In step S501, the control unit 10 transmits rectangular waves of frequency 40 kHz/Duty 50% to the transmission control unit 50 for a time interval of 125 μsec. In step S502, the control unit 10 stores a reception waveform received by the ultrasonic wave reception unit 40b in the reception waveform memory 513. In step S503, the control unit 10 transmits rectangular waves of frequency 45 kHz/Duty 50% to the transmission control unit 50 for a time interval of 111 μsec. In step S504, the control unit 10 stores a reception waveform received by the ultrasonic wave reception unit 40b in the reception waveform memory 513.

In the processing in steps S505 through S509, the control unit 10 controls the time difference calculation unit 514 to calculate the shift time of the peak. The control processing is described below with reference to FIGS. 16A and 16B. FIG. 16A illustrates waveform data stored when the ultrasonic wave transmission unit 40a is driven at the 40 kHz frequency. FIG. 16B illustrates waveform data stored when the ultrasonic wave transmission unit 40a is driven at the 45 kHz frequency.

In step S505, the control unit 10 calculates a peak (P4 illustrated in FIG. 16A) of the wave that corresponds to a predetermined number of times (n=4), in which "n" represents the number of times that the detection signal has exceeded a threshold value (V1 illustrated in FIG. 16A), when the ultrasonic wave transmission unit 40a is driven at the 40 kHz frequency. In step S506, the control unit 10 calculates a time interval (T14) that is required for the peak P4 to reach the ultrasonic wave reception unit 40b since the drive start timing.

In step S507, the control unit 10 detects a peak (P5 illustrated in FIG. 16A) of the wave that has lastly reached the ultrasonic wave reception unit 40b in the time interval T14 based on the data acquired when the driving frequency is 45 kHz. The time interval T14 since the drive start timing is defined as a "45 kHz peak detection window." In step S508, the control unit 10 calculates a time interval (T15) that is required for the peak P5 to reach the ultrasonic wave reception unit 40b since the drive start timing. In step S509, the control unit 10 calculates a time difference (T14−T15) that represents the shift time of the peak (i.e., 11.81 μsec in FIG. 16B).

In step S510, the control unit 10 determines that the detected wave is the fifth wave based on the shift time of the peak calculated in step S509 with reference to Table 1 stored in the peak calculation unit 515. In step S511, the control unit 10 calculates a time difference (−25 μsec) relative to the peak position of the fourth wave with reference to Table 1.

In step S512, the control unit 10 calculates a peak value of the fourth wave with reference to the calculated time difference, from the waveform stored in the reception waveform memory 513 when the driving frequency is 40 kHz. In step S513, the control unit 10 stores the calculated peak value of the fourth wave in the storage unit 101. In the present exemplary embodiment, the threshold value V1 illustrated in FIG. 16A is set in such a way as to surely detect respective peaks of the first to seventh waves even when the environment (e.g., temperature or humidity) is variable, as described with reference to FIG. 7 in the first exemplary embodiment.

Figure 17:
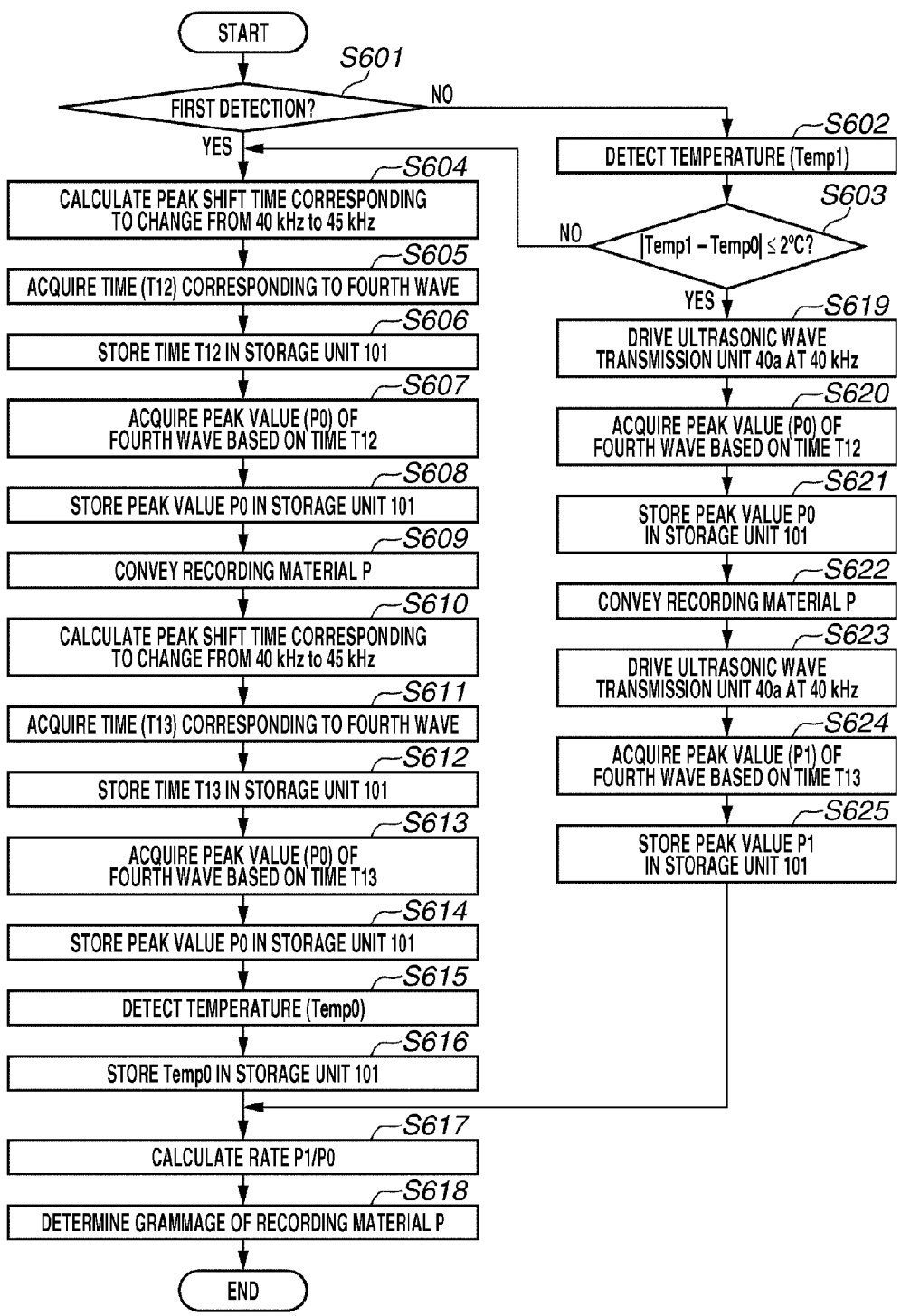
FIG. 17 is a flowchart illustrating detection control using ultrasonic waves according to the fourth exemplary embodiment.

FIG. 17 is a flowchart illustrating detection control using ultrasonic waves according to the present exemplary embodiment. An example of the control described with reference to FIG. 17 is control for detecting the above-described peak of the fourth wave in response to a change in the ambient environment. According to the present exemplary embodiment, an environmental change is used as a condition for performing the detection control, however, it is also useful to refer to the detection time as the condition as described in the first exemplary embodiment.

In step S601, the control unit 10 determines whether the present detection is the first detection after the power source is turned on. If it is determined that the present detection is not the first detection (NO in step S601), then in step S602, the control unit 10 acquires the temperature (Temp1) of the image forming apparatus from the environment sensor 64.

In step S603, the control unit 10 determines whether a difference between the temperature (Temp1) acquired in step S602 and the ambient temperature (Temp0) when the peak of the fourth wave is detected is equal to or less than two degrees. The determination condition in step S603 is not limited to the above-described example (i.e., two degrees). For example, an appropriate value can be set according to a user setting. If it is determined that the temperature difference is greater than 2 degrees (NO in step S603), the control unit 10 performs control to detect the peak position of the fourth wave in step S604 and subsequent steps.

In step S604, the control unit 10 calculates the shift time of the peak when the driving frequency of the ultrasonic wave transmission unit 40a is changed from 40 kHz to 45 kHz in the state where the recording material P is not present. In step S605, the control unit 10 detects a time interval (T12) between the drive start timing and the fourth-wave peak detection timing, when the frequency is 40 kHz, based on the shift time obtained in step S604.

In step S606, the control unit 10 stores the detected time interval T12 in the storage unit 101. In step S607, the control unit 10 extracts the peak value (P0) of the fourth wave from the reception waveform acquired at the 40 kHz frequency, with reference to the time interval T12. In step S608, the control unit 10 stores the detected peak value P0 in the storage unit 101.

In step S609, the control unit 10 causes the paper feeding roller 23 to convey the recording material P to the space between the ultrasonic wave transmission unit 40a and the ultrasonic wave reception unit 40b. In step S610, the control unit 10 changes the driving frequency of the ultrasonic wave transmission unit 40a from 40 kHz to 45 kHz in the state where the recording material P is present, and calculates the shift time of the peak. In step S611, the control unit 10 detects a time interval (T13) between the drive start timing and the fourth-wave peak detection timing, when the frequency is 40 kHz, based on the shift time obtained in step S610. In step S612, the control unit 10 stores the detected time interval T13 in the storage unit 101.

In step S613, the control unit 10 extracts a peak value (P1) of the fourth wave from the reception waveform acquired at the 40 kHz frequency, with reference to the time interval T13. In step S614, the control unit 10 stores the detected peak value P1 in the storage unit 101. In step S615, the control unit 10 acquires the ambient temperature (Temp0) of the image forming apparatus from the environment sensor 64. In step S616, the control unit 10 stores the acquired temperature Temp0 in the storage unit 101.

In step S617, the control unit 10 calculates the rate P1/P0 and stores the calculation result in the storage unit 101. In step S618, the control unit 10 determines the grammage of the recording material P based on the calculated rate P1/P0 with reference to the graph illustrating the relationship between the grammage and the transmittance in FIG. 9.

If it is determined that the present detection is not the first detection (NO in step S601) and it is determined that the temperature variation is equal to or less than two degrees (YES in step S603), the control unit 10 performs control processing in step S619 and subsequent steps. In step S619, the control unit 10 drives the ultrasonic wave transmission unit 40a at the 40 kHz frequency in the state where the recording material P is not present.

In step S620, the control unit 10 detects the peak value (P0) of the fourth wave with reference to the time interval (T12) between the drive start timing and the fourth-wave peak detection timing stored in step S606. In step S621, the control unit 10 stores the detected peak value P0 in the storage unit 101.

In step S622, the control unit 10 causes the paper feeding roller to convey the recording material P to the space between the ultrasonic wave transmission unit 40a and the ultrasonic wave reception unit 40b. In step S623, the control unit 10 drives the ultrasonic wave transmission unit 40a at the 40 kHz frequency in the state where the recording material P is present.

In step S624, the control unit 10 detects the peak value (P1) of the fourth wave with reference to the time interval (T13) between the drive start timing and the fourth-wave peak detection timing stored in step S612. In step S625, the control unit 10 stores the detected peak value (P1) of the fourth wave in the storage unit 101.

In step S617, the control unit 10 calculates the rate P1/P0 and stores the calculation result in the storage unit 101. In step S618, the control unit 10 determines the grammage of the recording material P based on the calculated rate P1/P0 with reference to the graph illustrating the relationship between the grammage and the transmittance in FIG. 9.

As described above, it is feasible to select a target wave from which the shift time of the peak is obtained with reference to the number of times the detection signal exceeds the predetermined threshold value. Accordingly, the detection method according to the present exemplary embodiment can accurately calculate the detection timing of the predetermined n-th wave. Therefore, the detection method according to the present exemplary embodiment enables the ultrasonic wave detection apparatus to accurately obtain the detection timing of the reception signal and accurately perform the grammage detection without performing any correction according to the environment. Further, because no correction according to the environment is performed, the detection method according to the present exemplary embodiment can reduce the load of the control unit 10. Furthermore, because no correcting operation is performed as a preparation operation, the time required for the correction operation can be reduced in the entire detection time.

In the above-described first to third exemplary embodiments, the factor used in selecting the target wave from which the shift time of the peak is obtained is the "time." According to a fifth exemplary embodiment, a target wave is selected based on a "zero-crossing timing of an ultrasonic wave reception signal" instead of the "time". Descriptions of the configuration similar to that described in the first to third exemplary embodiments are not repeated.

Figure 18A:
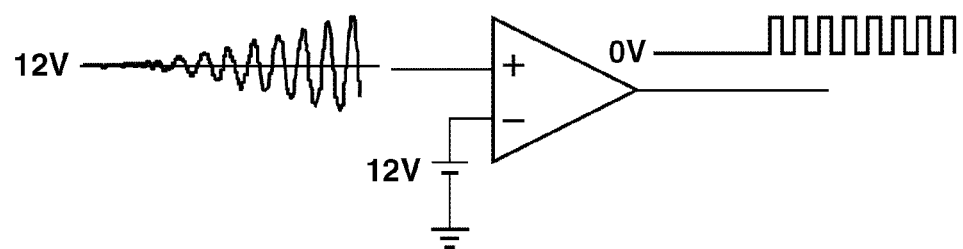
FIGS. 18A and 18B illustrate wave usable to detect a shift time of zero-crossing timing.
Figure 18B:
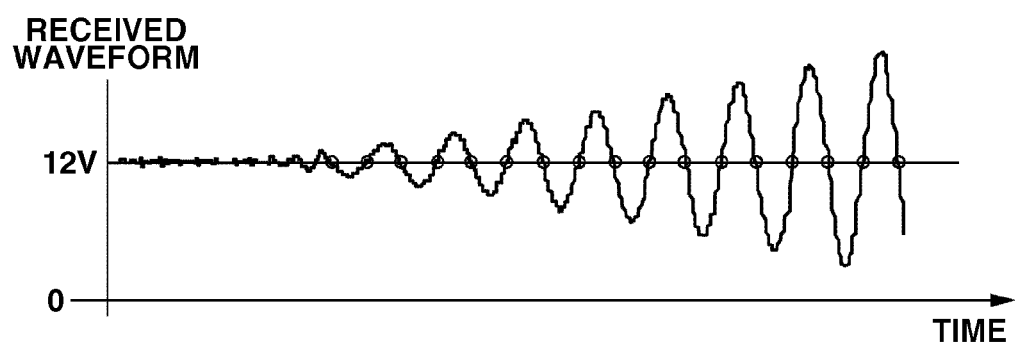

As illustrated in FIG. 18A, the output waveform of the ultrasonic wave reception unit 40b is obtained by superimposing a sine wave whose amplitude increases as the time elapses on DC 12V. The zero-crossing timing (indicated by circles "○" in FIG. 18B) is the timing that corresponds to phase angles 0° and 180° of sine wave.

Figure 19:
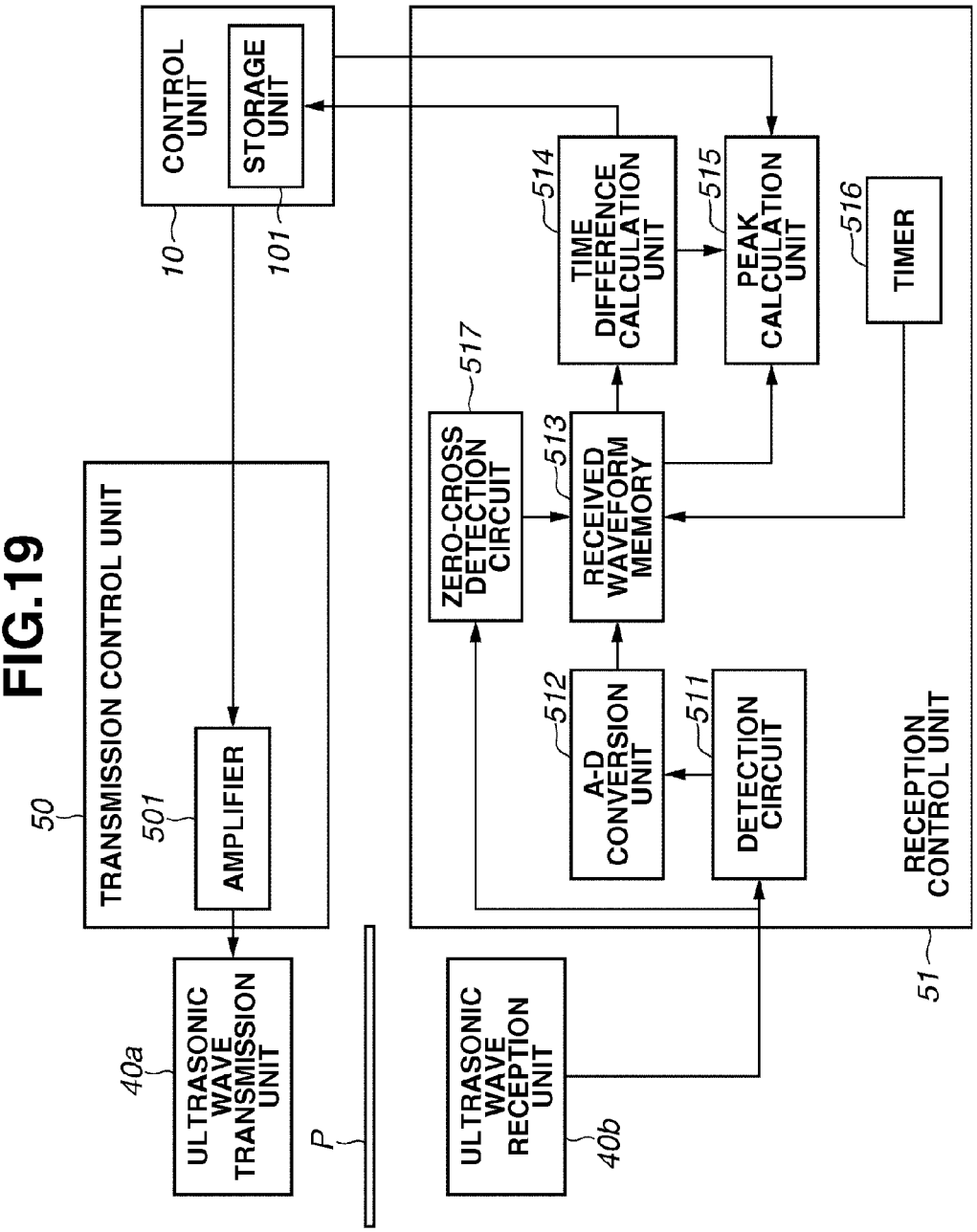
FIG. 19 is a control block diagram illustrating an ultrasonic wave detection unit according to a fifth exemplary embodiment of the present invention.

FIG. 19 is a control block diagram according to the present exemplary embodiment, which includes a zero-crossing detection circuit 517 in addition to the constituent components described in the first exemplary embodiment in FIG. 2. As illustrated in FIG. 18A, the zero-crossing detection circuit 517 is configured to compare the output waveform of the ultrasonic wave reception unit 40b with DC 12V and generate rectangular waves based on the comparison. The reception waveform memory 513 stores the output of the zero-crossing detection circuit 517.

Figure 20:
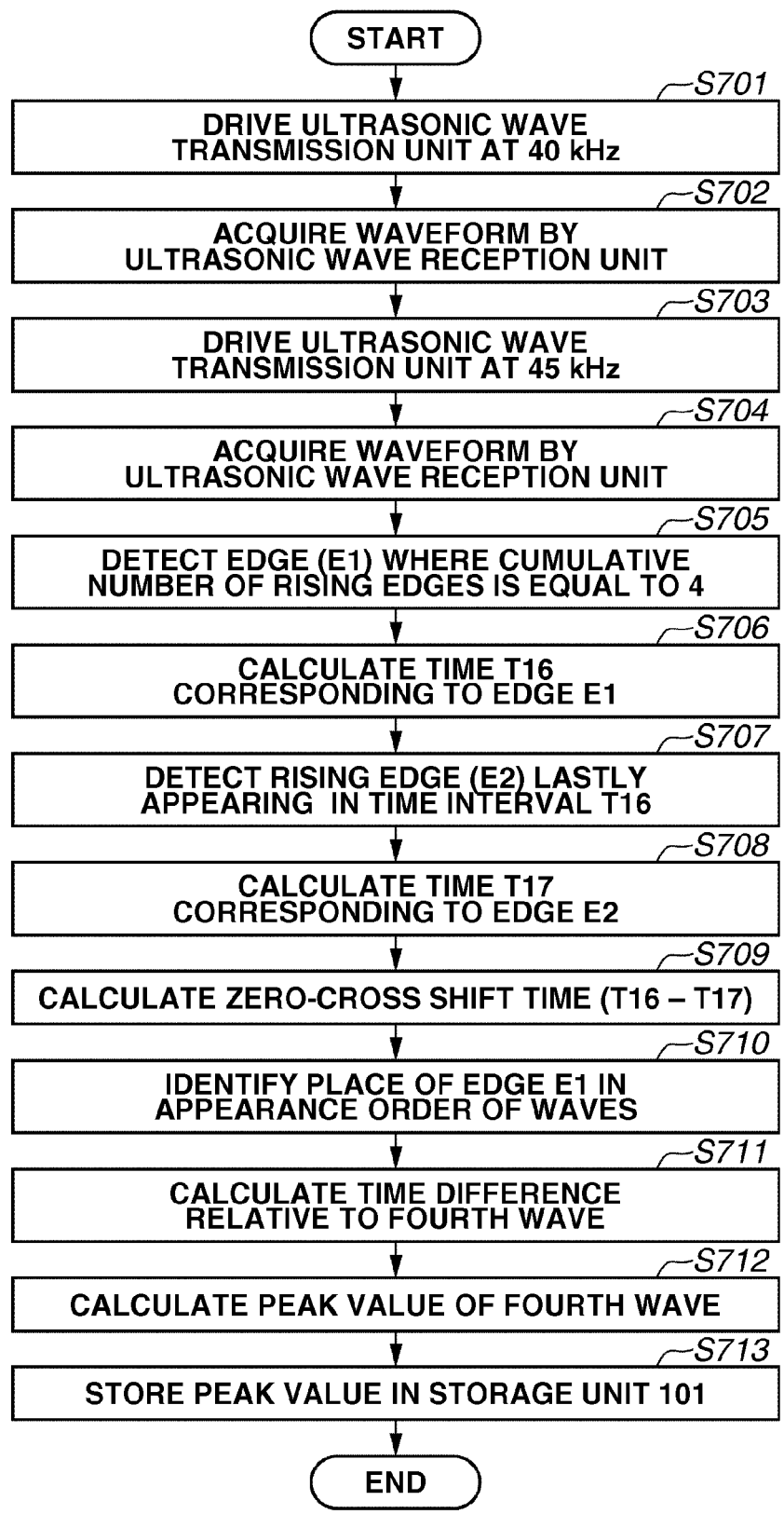
FIG. 20 is a flowchart illustrating a control sequence for calculating a peak of the fourth wave according to the fifth exemplary embodiment.

FIG. 20 is a flowchart illustrating a control sequence for calculating a peak of the fourth wave according to the present exemplary embodiment. In step S701, the control unit 10 transmits rectangular waves of frequency 40 kHz/Duty 50% to the transmission control unit 50 for a time interval of 125 μsec. In step S702, the control unit 10 stores a reception waveform received by the ultrasonic wave reception unit 40b in the reception waveform memory 513.

In step S703, the control unit 10 transmits rectangular waves of frequency 45 kHz/Duty 50% to the transmission control unit 50 for a time interval of 111 μsec. In step S704, the control unit 10 stores a reception waveform received by the ultrasonic wave reception unit 40b in the reception waveform memory 513.

Figure 21A:
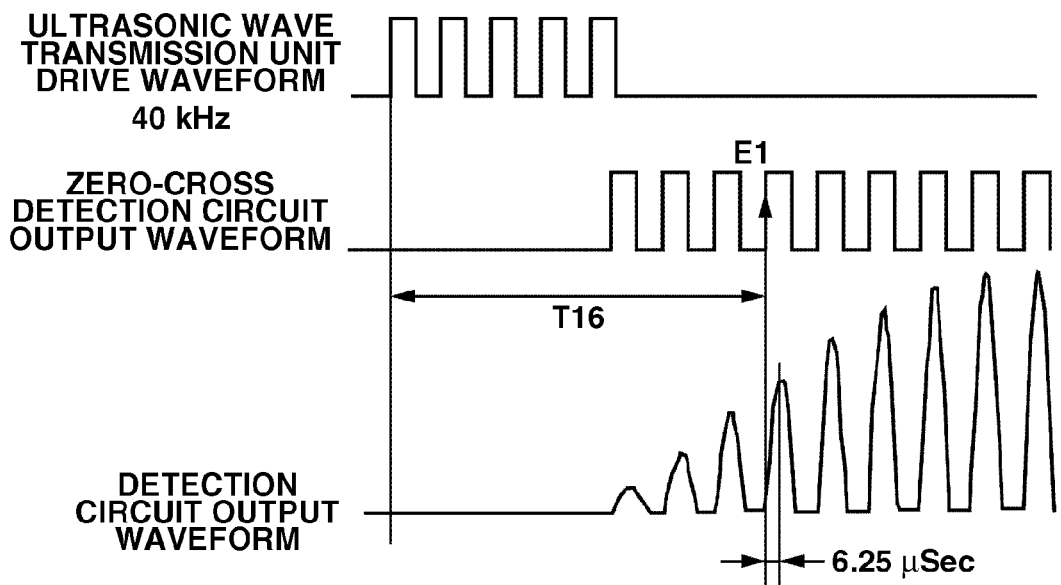
FIGS. 21A and 21B illustrate frequency changes in a waveform received when ultrasonic waves are transmitted at the 40 kHz frequency and in an output waveform received when ultrasonic waves are transmitted at the 45 kHz frequency according to the fifth exemplary embodiment.
Figure 21B:
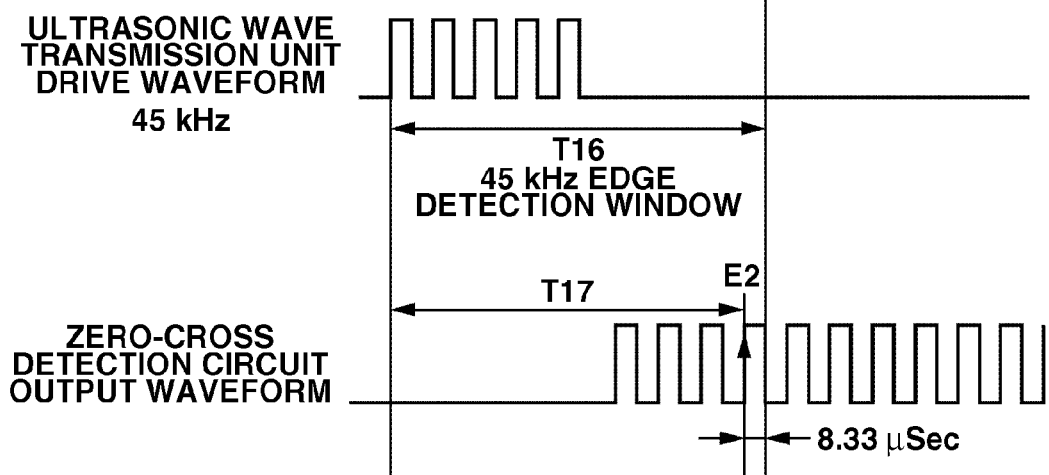

In the processing in steps S705 through S709, the control unit 10 controls the time difference calculation unit 514 to calculate the zero-crossing shift time. The control processing is described below with reference to FIGS. 21A and 21B. FIG. 21A illustrates waveform data stored when the ultrasonic wave transmission unit 40a is driven at the 40 kHz frequency. FIG. 21B illustrates waveform data stored when the ultrasonic wave transmission unit 40a is driven at the 45 kHz frequency.

In step S705, the control unit 10 detects a rising edge E1 where the count number "n" of rising edges appearing on the output waveform of the zero-crossing detection circuit 517 becomes equal to 4, when the ultrasonic wave transmission unit 40*a* is driven at the 40 kHz frequency. In step S706, the control unit 10 detects a time interval T16 between the drive start timing and the rising edge E1. In step S707, the control unit 10 detects a rising edge E2 that has lastly appeared in the time interval T16 since the drive start timing.

In step S708, the control unit 10 detects a time interval T17 between the drive start timing and the detection timing of the edge E2. The time interval T16 since the drive start timing is defined as a "45 kHz edge detection window." In step S709, the control unit 10 calculates a time difference (T16–T17) that represents the shift time of the zero-crossing timing (8.33 µsec illustrated in FIG. 21B). In step S710, the control unit 10 determines that the detected edge is the fourth wave based on the zero-crossing shift time obtained in step S709 with reference to Table 4 stored in the peak calculation unit 515.

In step S711, the control unit 10 calculates a time difference (6.25 µsec) relative to the peak position of the fourth wave. In step S712, the control unit 10 calculates a peak value of the fourth wave with reference to the calculated time difference, from the waveform stored in the reception waveform memory 513 when the driving frequency is 40 kHz. In step S713, the control unit 10 stores the calculated peak value of the fourth wave in the storage unit 101.

TABLE 4

| n-th wave | shift time | time difference relative to peak of fourth wave |
|---|---|---|
| 2nd wave | 2.78 µSec | 56.25 µSec |
| 3rd wave | 5.56 µSec | 31.25 µSec |
| 4th wave | 8.33 µSec | 6.25 µSec |
| 5th wave | 11.11 µSec | −18.75 µSec |
| 6th wave | 13.89 µSec | −43.75 µSec |
| 7th wave | 16.67 µSec | −68.75 µSec |

Figure 22A:
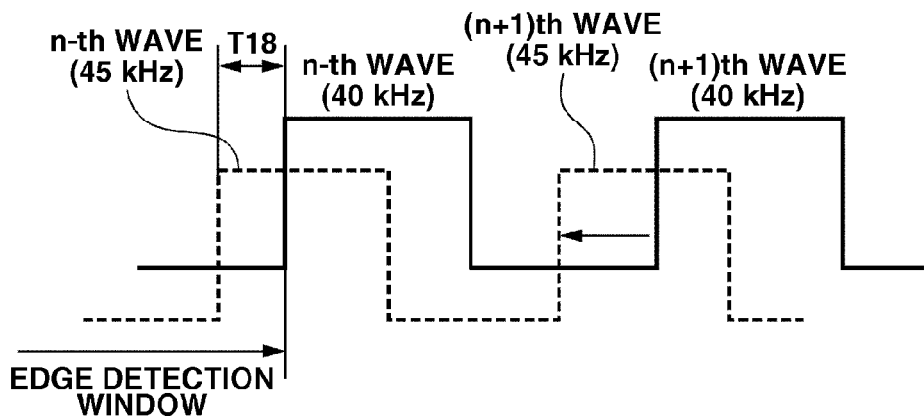
FIGS. 22A to 22C illustrate waves usable to obtain a shift time of zero-crossing timing.
Figure 22B:
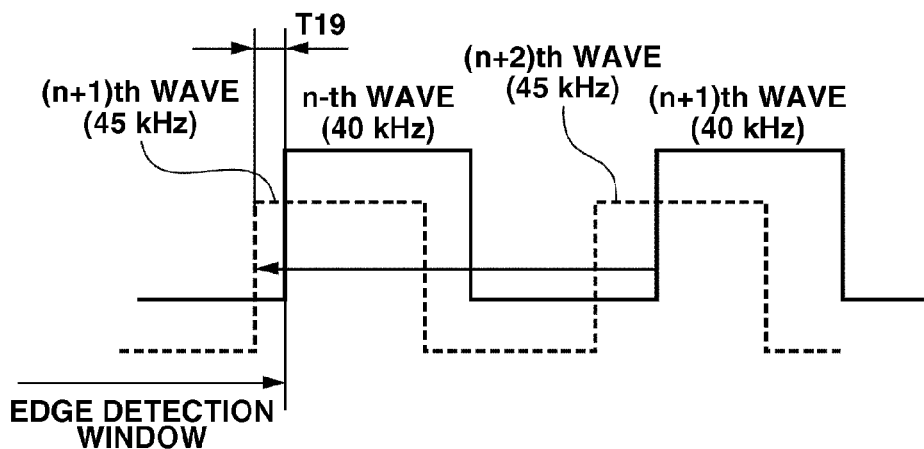
Figure 22C:
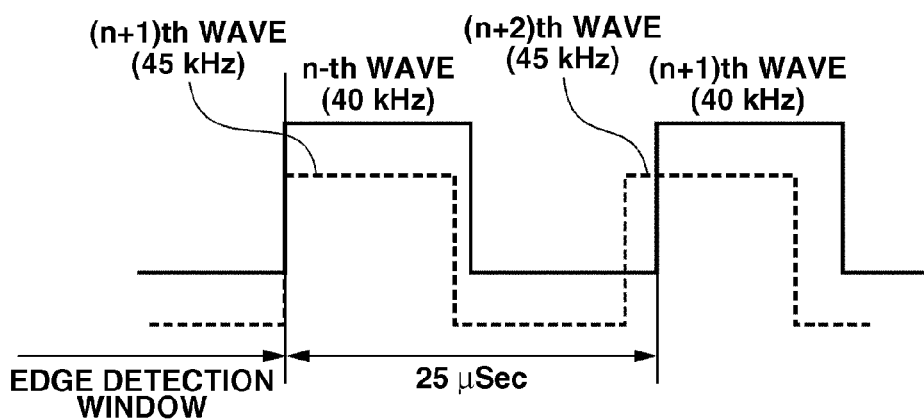

In the present exemplary embodiment, the waves used to obtain the shift time of the zero-crossing timing are the first to ninth waves. The reason is described below with reference to output waveforms obtainable when the ultrasonic wave transmission unit 40*a* is driven at the 40 kHz frequency and output waveforms obtainable when the ultrasonic wave transmission unit 40*a* is driven at the 45 kHz frequency as illustrated in FIGS. 22A to 22C. In FIGS. 22A to 22C, the solid lines indicate the output waveforms of 40 kHz ultrasonic waves, and the dotted lines indicate the output waveforms of 45 kHz ultrasonic waves.

FIG. 22A indicates a state where a rising edge of the n-th wave is present in the "45 kHz edge detection window" when the ultrasonic wave transmission unit 40*a* is driven at the 45 kHz frequency. In this state, the time difference calculation unit 514 can calculate a time difference (T18) in the rising edge of the same n-th wave of the output waveform between the 40 kHz driving operation and the 45 kHz driving operation.

FIG. 22B indicates a state where a rising edge of the (n+1)-th wave is present in the "45 kHz edge detection window" when the ultrasonic wave transmission unit 40*a* is driven at the 45 kHz frequency. In this state, the time difference calculation unit 514 calculates a time difference (T19) between the rising edge of the n-th wave of the output waveform in the 40 kHz driving operation and the rising edge of the (n+1)-th wave of the output waveform in the 45 kHz driving operation. Thus, the time difference calculation unit 514 fails in detection because the time difference calculation unit 514 cannot compare the rising edges of the same wave number.

Hence, in the present exemplary embodiment, the rising edge shift time is set to be less than 25 µsec so that the (n+1)-th wave in the 45 kHz driving operation can be excluded from the "45 kHz edge detection window", as illustrated in FIG. 22C. When the peak shift time of each wave number is checked, the peak shift time of the tenth wave is 25 µsec. In other words, the tenth wave cannot be detected because the above-described condition "less than 25 µsec" cannot be satisfied. Accordingly, using the first to ninth waves in detecting the shift time of the zero-crossing timing is useful to eliminate an error detection that may occur when the n-th wave is compared with the (n+1)-th wave.

As described above, the shift time of the zero-crossing timing is usable in selecting a target wave to be used to obtain the shift time of the peak. Accordingly, the detection method according to the present exemplary embodiment can accurately calculate the detection timing of the predetermined n-th wave. Therefore, the detection method according to the present exemplary embodiment enables the ultrasonic wave detection apparatus to accurately obtain the detection timing of the reception signal and accurately perform the grammage detection without performing any correction according to the environment. Further, because no correction according to the environment is performed, the detection method according to the present exemplary embodiment can reduce the load of the control unit 10. Furthermore, because no correcting operation is performed as a preparation operation, the time required for the correction operation can be reduced in the entire detection time.

In a sixth exemplary embodiment, the detection timing of the predetermined n-th wave is described. A method which performs an initial sequence when the power source is turned on and a detection sequence in restoration from an energy saving mode is described as an example according to the present exemplary embodiment. Descriptions of the configuration similar to that described in the first to fifth exemplary embodiments are not repeated.

Figure 23:
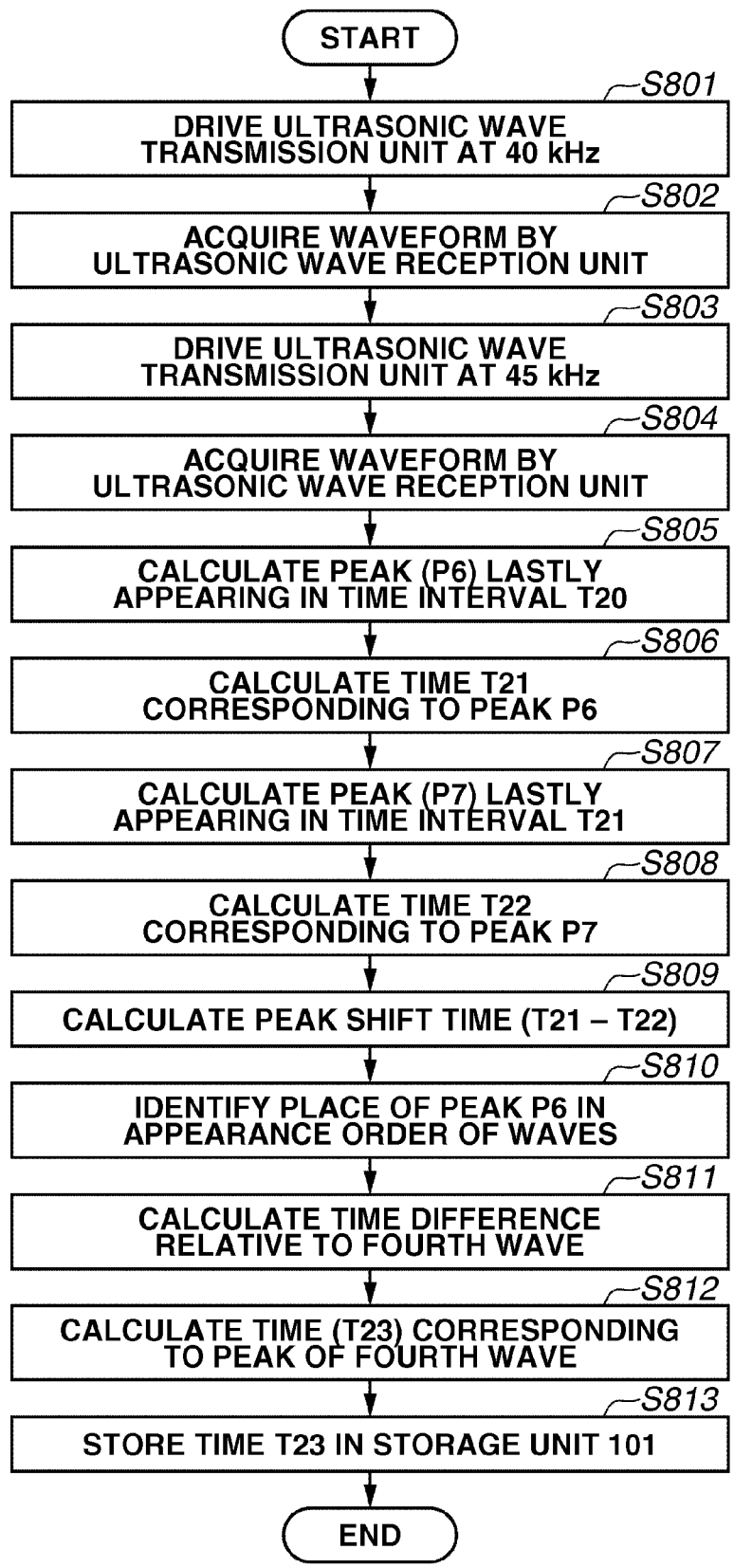
FIG. 23 is a flowchart illustrating a control sequence for calculating a peak of the fourth wave according to a sixth exemplary embodiment of the present invention.

FIG. 23 is a flowchart illustrating control to detect a peak position of the fourth wave in the power-ON initial sequence or in the restoration from the energy saving mode. In step S801, the control unit 10 transmits rectangular waves of frequency 40 kHz/Duty 50% to the transmission control unit 50 for a time interval of 125 µsec. In step S802, the control unit 10 stores a reception waveform received by the ultrasonic wave reception unit 40*b* in the reception waveform memory 513.

In step S803, the control unit 10 transmits rectangular waves of frequency 45 kHz/Duty 50% to the transmission control unit 50 for a time interval of 111 µsec. In step S804, the control unit 10 stores a reception waveform received by the ultrasonic wave reception unit 40*b* in the reception waveform memory 513.

Figure 24A:
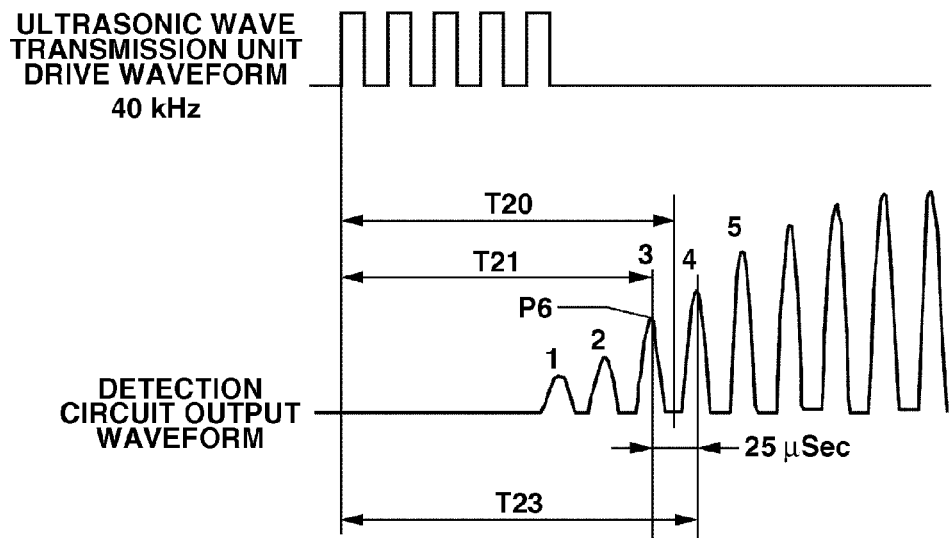
FIGS. 24A and 24B illustrate frequency changes in a waveform received when ultrasonic waves are transmitted at the 40 kHz frequency and in an output waveform received when ultrasonic waves are transmitted at the 45 kHz frequency according to the sixth exemplary embodiment.
Figure 24B:
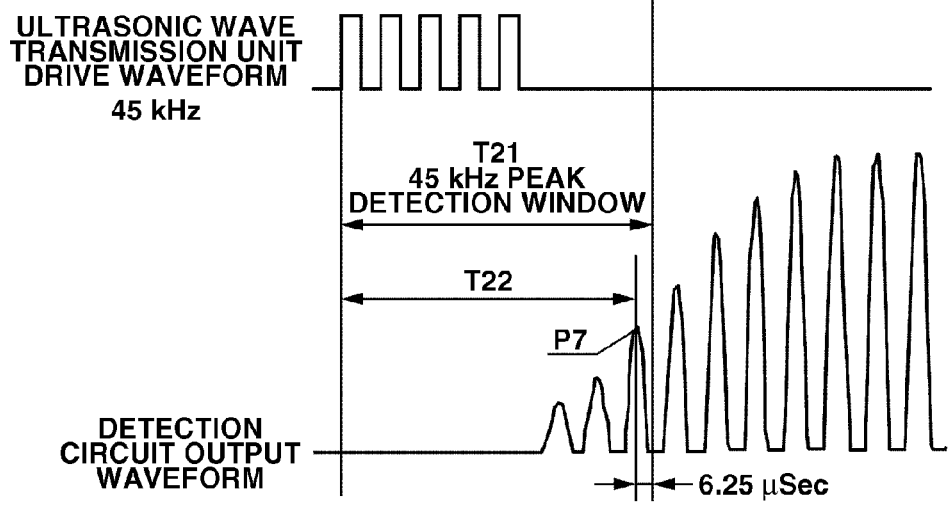

In the processing in steps S805 through S809, the control unit 10 controls the time difference calculation unit 514 to calculate the shift time of the peak. The control processing is described below with reference to FIGS. 24A and 24B. FIG. 24A illustrates waveform data stored when the ultrasonic wave transmission unit 40*a* is driven at the 40 kHz frequency. FIG. 24B illustrates waveform data stored when the ultrasonic wave transmission unit 40*a* is driven at the 45 kHz frequency.

In step S805, the control unit 10 calculates a peak (P6 illustrated in FIG. 24A) of the wave that has lastly reached the ultrasonic wave reception unit 40*b* in a time interval T20 since the drive start timing of the ultrasonic wave transmission unit 40*a* when the ultrasonic wave transmission unit 40*a* is driven at the 40 kHz frequency. In step S806, the control unit 10 calculates a time interval (T21) that is required for the peak P6 to reach the ultrasonic wave reception unit 40b since the drive start timing of the ultrasonic wave transmission unit 40a.

In step S807, the control unit 10 calculates a peak (P7 illustrated in FIG. 24A) of the wave that has lastly reached the ultrasonic wave reception unit 40b in the time interval T21 when the ultrasonic wave transmission unit 40a is driven at the 45 kHz frequency. In the present exemplary embodiment, the time interval T21 since the drive start timing of the ultrasonic wave transmission unit 40a is defined as a "45 kHz peak detection window."

In step S808, the control unit 10 calculates a time interval (T22) that is required for the peak P7 to reach the ultrasonic wave reception unit 40b since the drive start timing of the ultrasonic wave transmission unit 40a. In step S809, the control unit 10 calculates a time difference (T21−T22) that represents the shift time of the peak (i.e., 6.25 μsec in FIG. 24B).

In the present exemplary embodiment, the method for calculating the peak of the lastly reached wave in the predetermined time interval T20 since the drive start timing of the ultrasonic wave transmission unit 40a is described an example, although the method according to the present exemplary embodiment is not limited to the above-described example. For example, it is feasible to calculate a peak of the wave that appears firstly after the elapse of the time interval T20 and calculate the shift time of the peak value according to a method similar to the above-described method.

In step S810, the control unit 10 determines that the detected wave is the third wave based on the shift time of the peak obtained in step S809 with reference to Table 1 stored in the peak calculation unit 515. In step S811, the control unit 10 calculates a time difference (25 μsec) relative to the peak position of the fourth wave with reference to Table 1. In step S812, the control unit 10 calculates a time interval T23 between the drive start timing of the ultrasonic wave transmission unit 40a and the fourth-wave peak detection timing based on the calculated time difference.

In step S813, the control unit 10 stores the calculated time interval T23 in the storage unit 101. When the control unit 10 detects the grammage of the recording material P in an image forming operation, the control unit 10 detects the peak value of the fourth wave based on the time interval T23 in the state where the recording material P is not present. As described in the preceding exemplary embodiments, when a predetermined time has elapsed since the time interval T23 is acquired, or when there is any variation in the environment, the control unit 10 can detect the time interval T23 again to detect the grammage of the recording material P.

As described above, the detection method according to the present exemplary embodiment performs control to calculate the detection timing of the predetermined n-th wave beforehand in the power-ON initial sequence or in the restoration from the energy saving mode. Accordingly, the detection method according to the present exemplary embodiment can accurately calculate the detection timing of the predetermined n-th wave. Therefore, the detection method according to the present exemplary embodiment enables the ultrasonic wave detection apparatus to accurately obtain the detection timing of the reception signal and accurately perform the grammage detection without performing any correction according to the environment. Further, because no correction according to the environment is performed, the detection method according to the present exemplary embodiment can reduce the load of the control unit 10. Furthermore, because no correcting operation is performed as a preparation operation, the time required for the correction operation can be reduced in the entire detection time.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2011-180546 filed Aug. 22, 2011, which is hereby incorporated by reference herein in its entirety.

What is claimed is:

1. An ultrasonic wave detection apparatus comprising:
a transmission unit configured to transmit ultrasonic waves at a first frequency and ultrasonic waves at a second frequency that is higher than the first frequency;
a reception unit configured to receive the ultrasonic waves at the first frequency transmitted by the transmission unit and output a first signal including a first plurality of peak values corresponding to the ultrasonic waves at the first frequency being received, and receive the ultrasonic waves at the second frequency transmitted by the transmission unit and output a second signal including a second plurality of peak values corresponding to the ultrasonic waves at the second frequency being received; and
a control unit configured to calculate a first time interval from when the transmission unit transmits the ultrasonic waves at the first frequency to when a predetermined peak value in the first plurality of peak values is obtained, and a second time interval from when the transmission unit transmits the ultrasonic waves at the second frequency to when a peak value in the second plurality of peak values is lastly obtained during the first time interval,
wherein the control unit detects a position of the predetermined peak value in the order of the first plurality of peak values based on a time difference between the first time interval and the second time interval; and
wherein a grammage of the recording material is determined based on the detected position of the predetermined peak value or image forming conditions of an image forming unit are controlled based on the detected position of the predetermined peak value.

2. The ultrasonic wave detection apparatus according to claim 1,
wherein, after the predetermined peak value in the first plurality of peak values is detected as a peak value of a n-th wave, the control unit calculates a timing to obtain a peak value of a m-th wave in the first plurality of peak values that is different from the n-th wave.

3. The ultrasonic wave detection apparatus according to claim 2,
wherein the ultrasonic wave detection apparatus is configured to detect a recording material,
wherein the control unit determines a grammage of a recording material based on a ratio between a peak value of the m-th wave in the first plurality of peak values that is obtained in a state where no recording material exists between the transmission unit and the reception unit, and a peak value of the m-th wave in the first plurality of peak values that is obtained in a state where the recording material exists between the transmission unit and the reception unit.

4. The ultrasonic wave detection apparatus according to claim 2,
wherein the ultrasonic wave detection apparatus is configured to detect a recording material, wherein the control unit determines whether a recording material is double fed or not based on a ratio between a peak value of the m-th wave in the first plurality of peak values that is obtained in a state where no recording material exists between the transmission unit and the reception unit, and a peak value of the m-th wave in the first plurality of peak values that is obtained in a state where the recording material exists between the transmission unit and the reception unit.

5. The ultrasonic wave detection apparatus according to claim 1,
wherein the control unit extracts a peak value that is lastly obtained during a time interval from when the transmission unit transmits the ultrasonic waves at the first frequency to when the predetermined time passes, as the predetermined peak value in the first plurality of peak values.

6. A recording material determination apparatus comprising:
a transmission unit configured to transmit ultrasonic waves at a first frequency and ultrasonic waves at a second frequency that is higher than the first frequency;
a reception unit configured to receive the ultrasonic waves at the first frequency transmitted by the transmission unit and output a first signal including a first plurality of peak values corresponding to the ultrasonic waves at the first frequency being received, and receive the ultrasonic waves at the second frequency transmitted by the transmission unit and output a second signal including a second plurality of peak values corresponding to the ultrasonic waves at the second frequency being received; and
a control unit configured to calculate a first time interval from when the transmission unit transmits the ultrasonic waves at the first frequency to when a predetermined peak value in the first plurality of peak values is obtained, and a second time interval from when the transmission unit transmits the ultrasonic waves at the second frequency to when a peak value in the second plurality of peak values is lastly obtained during the first time interval,
wherein the control unit detects a position of the predetermined peak value in the order of the first plurality of peak values based on a time difference between the first time interval and the second time interval, and
wherein the control unit determines a grammage of the recording material based on the predetermined peak value that is obtained in a state where the recording material exists between the transmission unit and the reception unit.

7. The recording material determination apparatus according to claim 6,
wherein the control unit determines the grammage of the recording material based on a ratio between the predetermined peak value that is obtained in a state where no recording material exists between the transmission unit and the reception unit, and the predetermined peak value that is obtained in the state where the recording material exists between the transmission unit and the reception unit.

8. The recording material determination apparatus according to claim 6,
wherein the control unit extracts a peak value that is lastly obtained during a time interval from when the transmission unit transmits the ultrasonic waves at the first frequency to when the predetermined time passes, as the predetermined peak value in the first plurality of peak values.

9. An image forming apparatus comprising:
an image forming unit configured to form an image on a recording material;
a transmission unit configured to transmit ultrasonic waves at a first frequency and ultrasonic waves at a second frequency that is higher than the first frequency;
a reception unit configured to receive the ultrasonic waves at the first frequency transmitted by the transmission unit and output a first signal including a first plurality of peak values corresponding to the ultrasonic waves at the first frequency being received, and receive the ultrasonic waves at the second frequency transmitted by the transmission unit and output a second signal including a second plurality of peak values corresponding to the ultrasonic waves at the second frequency being received; and
a control unit configured to calculate a first time interval from when the transmission unit transmits the ultrasonic waves at the first frequency to when a predetermined peak value in the first plurality of peak values is obtained, and a second time interval from when the transmission unit transmits the ultrasonic waves at the second frequency to when a peak value in the second plurality of peak values is lastly obtained during the first time interval,
wherein the control unit detects a position of the predetermined peak value in the order of the first plurality of peak values based on a time difference between the first time interval and the second time interval, and
wherein the control unit controls image forming conditions of the image forming unit based on the predetermined peak value that is obtained in a state where the recording material exists between the transmission unit and the reception unit.

10. The image forming apparatus according to claim 9,
wherein the control unit controls the image forming conditions based on a ratio between the peak value of a wave in specific order in the first plurality of peak values that is obtained in a state where no recording material exists between the transmission unit and the reception unit, and the peak value of a wave in specific order in the first plurality of peak values that is obtained in a state where the recording material exists between the transmission unit and the reception unit.

11. The image forming apparatus according to claim 9,
wherein the control unit extracts a peak value that is lastly obtained during a time interval from when the transmission unit transmits the ultrasonic waves at the first frequency to when the predetermined time passes, as the predetermined peak value in the first plurality of peak values.

12. An ultrasonic wave detection apparatus comprising:
a transmission unit configured to transmit ultrasonic waves at a first frequency and ultrasonic waves at a second frequency that is lower than the first frequency;
a reception unit configured to receive the ultrasonic waves at the first frequency transmitted by the transmission unit and output a first signal including a first plurality of peak values corresponding to the ultrasonic waves at the first frequency being received, and receive the ultrasonic waves at the second frequency transmitted by the transmission unit and output a second signal including a second plurality of peak values corresponding to the ultrasonic waves at the second frequency being received; and a control unit configured to calculate a first time interval from when the transmission unit transmits the ultrasonic waves at the first frequency to when a predetermined peak value in the first plurality of peak values is obtained, and a second time interval from when the transmission unit transmits the ultrasonic waves at the second frequency to when a peak value in the second plurality of peak values is firstly obtained after the first time interval, wherein the control unit detects a position of the predetermined peak value in the order of the first plurality of peak values based on a time difference between the first time interval and the second time interval; and wherein a grammage of the recording material is determined based on the detected position of the predetermined peak value or image forming conditions of an image forming unit are controlled based on the detected position of the predetermined peak value.

13. The ultrasonic wave detection apparatus according to claim 12, wherein, after the predetermined peak value in the first plurality of peak values is detected as a peak value of a n-th wave, the control unit calculates a timing to obtain a peak value of a m-th wave in the first plurality of peak values that is different from the n-th wave.

14. The ultrasonic wave detection apparatus according to claim 13, wherein the ultrasonic wave detection apparatus is configured to detect a recording material, and wherein the control unit determines a grammage of the recording material based on a ratio between the peak value of the m-th wave in the first plurality of peak values that is obtained in a state where no recording material exists between the transmission unit and the reception unit, and the peak value of the m-th wave in the first plurality of peak values that is obtained in a state where the recording material exists between the transmission unit and the reception unit.

15. The ultrasonic wave detection apparatus according to claim 13, wherein the ultrasonic wave detection apparatus is configured to detect a recording material, wherein the control unit determines whether a recording material is double fed or not based on a ratio between the peak value of the m-th wave in the first plurality of peak values that is obtained in a state where no recording material exists between the transmission unit and the reception unit, and the peak value of the m-th wave in the first plurality of peak values that is obtained in a state where the recording material exists between the transmission unit and the reception unit.

16. The ultrasonic wave detection apparatus according to claim 12, wherein the control unit extracts a peak value that is lastly obtained during a time interval from when the transmission unit transmits the ultrasonic waves at the first frequency to when the predetermined time passes, as the predetermined peak value in the first plurality of peak values.

17. A recording material determination apparatus comprising:

a transmission unit configured to transmit ultrasonic waves at a first frequency and ultrasonic waves at a second frequency that is lower than the first frequency;

a reception unit configured to receive the ultrasonic waves at the first frequency transmitted by the transmission unit and output a first signal including a first plurality of peak values corresponding to the ultrasonic waves at the first frequency being received, and receive the ultrasonic waves at the second frequency transmitted by the transmission unit and output a second signal including a second plurality of peak values corresponding to the ultrasonic waves at the second frequency being received; and a control unit configured to calculate a first time interval from when the transmission unit transmits the ultrasonic waves at the first frequency to when a predetermined peak value in the first plurality of peak values is obtained, and a second time interval from when the transmission unit transmits the ultrasonic waves at the second frequency to when a peak value in the second plurality of peak values is lastly obtained during the first time interval, wherein the control unit detects a position of the predetermined peak value in the order of the first plurality of peak values based on a time difference between the first time interval and the second time interval, and wherein the control unit determines a grammage of the recording material based on the predetermined peak value that is obtained in a state where the recording material exists between the transmission unit and the reception unit.

18. The recording material determination apparatus according to claim 17, wherein the control unit determines a grammage of the recording material based on a ratio between the predetermined peak value that is obtained in a state where no recording material exists between the transmission unit and the reception unit, and the predetermined peak value that is obtained in the state where the recording material exists between the transmission unit and the reception unit.

19. The recording material determination apparatus according to claim 17, wherein the control unit extracts a peak value that is lastly obtained during a time interval from when the transmission unit transmits the ultrasonic waves at the first frequency until the predetermined time passes, as the predetermined peak value of the first signal.

20. An image forming apparatus comprising:

an image forming unit configured to form an image on a recording material;

a transmission unit configured to transmit ultrasonic waves at a first frequency and ultrasonic waves at a second frequency that is lower than the first frequency;

a reception unit configured to receive the ultrasonic waves at the first frequency transmitted by the transmission unit and output a first signal including a first plurality of peak values corresponding to the ultrasonic waves at the first frequency being received, and receive the ultrasonic waves at the second frequency transmitted by the transmission unit and output a second signal including a second plurality of peak values corresponding to the ultrasonic waves at the second frequency being received; and a control unit configured to calculate a first time interval from when the transmission unit transmits the ultrasonic waves at the first frequency to when a predetermined peak value in the first plurality of peak values is obtained, and a second time interval from when the transmission unit transmits the ultrasonic waves at the second frequency to when a peak value in the second plurality of peak values is lastly obtained during the first time interval, wherein the control unit detects a position of the predetermined peak value in the order of the first plurality of peak values based on a time difference between the first time interval and the second time interval, and wherein the control unit controls image forming conditions of the image forming unit based on the predetermined peak value that is obtained in a state where the recording material exists between the transmission unit and the reception unit.

21. The image forming apparatus according to claim 20, wherein the control unit controls the image forming conditions based on a ratio between the predetermined peak value that is obtained in a state where no recording material exists between the transmission unit and the reception unit, and the predetermined peak value that is obtained in the state where the recording material exists between the transmission unit and the reception unit.

22. The image forming apparatus according to claim 20, wherein the control unit extracts a peak value that is lastly obtained during a time interval from when the transmission unit transmits the ultrasonic waves at the first frequency until the predetermined time passes, as the predetermined peak value of the first signal.

\* \* \* \* \*